United States Patent
Rao

(10) Patent No.: US 9,163,262 B2
(45) Date of Patent: *Oct. 20, 2015

(54) IN VITRO AND IN VIVO DELIVERY OF GENES AND PROTEINS USING THE BACTERIOPHAGE T4 DNA PACKAGING MACHINE

(71) Applicant: The Catholic University of America, Washington, DC (US)

(72) Inventor: Venigalla B. Rao, Silver Spring, MD (US)

(73) Assignee: The Catholic University of America, Washington, DC (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/096,238

(22) Filed: Dec. 4, 2013

(65) Prior Publication Data

US 2014/0256796 A1   Sep. 11, 2014

Related U.S. Application Data

(60) Provisional application No. 61/774,895, filed on Mar. 8, 2013.

(51) Int. Cl.
*C12Q 1/68* (2006.01)
*C12N 15/87* (2006.01)

(52) U.S. Cl.
CPC ............ *C12N 15/87* (2013.01); *C07K 2319/10* (2013.01); *C07K 2319/40* (2013.01); *C07K 2319/61* (2013.01); *C12N 2795/10122* (2013.01); *C12N 2795/10123* (2013.01); *C12N 2795/10142* (2013.01); *C12N 2810/6009* (2013.01); *C12N 2810/85* (2013.01); *C12N 2810/859* (2013.01)

(58) Field of Classification Search
None
See application file for complete search history.

(56) References Cited

U.S. PATENT DOCUMENTS

| | | | | |
|---|---|---|---|---|
| 7,041,441 | B1 * | 5/2006 | Steven et al. ........... | 435/5 |
| 2005/0226892 | A1 | 10/2005 | Rao | |
| 2006/0029615 | A1 | 2/2006 | Ren et al. | |
| 2008/0274533 | A1 | 11/2008 | Alving et al. | |
| 2011/0250263 | A1 | 10/2011 | Rao | |

OTHER PUBLICATIONS de Wet et al. Firefly luciferase gene: structure and expression in mammalian cells. Mol Cell Biol. Feb. 1987;7(2):725-37.*
Li et al., "Assembly of the Small Outer Capsid Protein, Soc, on Bateriophage T4: a novel system for high density display of multiple large anthrax toxins and foreign proteins on phage capsid", J. Mol Biol., vol. 370, No. 5, pp. 1006-1019 (2007).
International Search Report and Written Opinion received in PCT Appln. No. PCT/IB2014/058716, mailed May 27, 2014.
Neumann, E, Schaefer-Ridder M, Wang Y, and Hofschneider PH Gene transfer into mouse lyoma cells by electroporation in high electric fields. EMBO J 1(7):841-45 (1982).
Kay MA State-of-the-art gene-based therapiues: the road ahead. Nat Rev Genet 12(5):316-328 (2011).
Demayo JL, Wang J, Liang D, Zhang R, and Demayo FH Genetically engineered mice by pronuclear DNA microinjection. Curr Protoc Mouse Biol 2:245-62 (2012).
Yan M, Du J, Gu Z, Liang M, Hu Y, Zhang W, Priceman S, Wu L, Zhou Zh, Liu Z et al. A novel intracellular protein delivery platform based on single-protein nanocapsules. Nat Nanotechnol 5(1):48-53 (2010).
Kaczmarczyk SJm Sitaraman K, Young HA, Hughes SH, and Chatterjee DK Protein delivery using engineered virus-like particles. Proc Natl Acad Sci U S A 108(41):16998-17003.
Smith DE, Tans SJ, Smith SB, Grimes S, Anderson DL, and Bustamante C The bacteriophage straight phi29 portal motor can package DNA against a large internal force. Nature 413(6857):748-52(2001).
Fuller DN, Raymer DM, Kottadiel VI, Rao VB and Smith DE Single phage T4 DNA packaging motor exhibit large force generation, high velocity, and dynamic variability. Proc Natl Acad Sci U S A 104(43):16868-73 (2007).
Casjens SR The DNA-packaging nanomotor of tailed bacteriophages. Nat Rev Microbiol 9(9):647-57 (2011).
Rao VB and Feiss M The bacteriophage DNA packaging motor. Annu Rev Genet 42:647-81 (2008).
Sun S, Kondabagil K, Draper B, Alam TI, Bowman VD, Zhang Z, Hegde S, Fokine A, Rossmann MG, and Rao VB The structure of the phage T4 DNA packaging motor suggests a mechanism dependent on electrostatic forces. Cell 135 (7):1251-62 (2008).
Fokine A, Chipman PR, Leiman PG, Mesyanzhinov W, Rao VB, and Rossmann MG Molecular architecture of the prolate head of bacteriophage T4. Proc Natl Acad Sci U S A 101(16):6003-08 (2004).
Black LW, Showe MK, and Steven AC Morphogenesis of the T4 Head, ed. Karam JD. American Society of Microbiology, Washington DC pp. 218-258 (1994).
Qin L, Fokine A, O'Donnell E, Rao VB, and Rossmann MG Structure of the small outer capsid protein, Soc: a clamp for stabilizing capsids of T4-like phages. J Mol Biol 395(4):728-41 (2010).
Fokine A, Islam MZ, Zhang Z, Bowman VD, Rao VB, and Rossmann MG Structure of the three N-terminal immunoglobulin domains of the highly immunogenic outer capsid protein from a T4-like bacteriophage. J Virol 85 (16):8141-48 (2011).
Ishii T and Yanagida M The two dispensable structural proteins (soc and hoc) of the T4 phage capsid; their purification and properties, isolation and characterization of the defective mutants, and their binding with the defective heads in vitro. J Mol Biol 109(4):487-514 (1977).
Li Q, Shivachandra SB, Leppla SH, and Rao VB Bacteriophage T4 capsid: a unique platform for efficient surface assembly of macromolecular complexes. J Mol Biol 363(2):577-88 (2006).

(Continued)

*Primary Examiner* — Michele K Joike
(74) *Attorney, Agent, or Firm* — Alchemy-Partners, PC

(57) ABSTRACT

Described is T4 DNA packaging machine comprising: one or more DNA molecules packaged in a head of the T4 DNA packaging machine, one or more Hoc-fused proteins displayed on the head of the T4 DNA packaging machine, and one or more Soc-fused proteins displayed on the head of the T4 DNA packaging machine. Also described are methods of making and using such a T4 DNA packaging machine.

20 Claims, 16 Drawing Sheets

(56) References Cited

OTHER PUBLICATIONS

Sathaliyawala T, Rao M, Maclean DM, Birx DL, Alving CR, and Rao VB Assembly of human immunodeficiency virus (HIV) antigens on bacteriophage T4: a novel in vitro approach to construct multicomponent HIV vaccines. J Virol 80 (15):7688-98 (2006).

Zhang Z, Kottadiel VI, Vafabakhsh R, Dai L, Chemla YR, Ha T, and Rao VB A promiscuous DNA packaging machine from bacteriophage T4. PLoS BIol 9(2):e1000592 (2011).

Leiman PG, Arisaka, F, van Raaig MJ, Kostyuchenko VA, Aksyuk AA, Kanamaru S, and Rossmann MG Morphogenesis of the T4 tail and tail fibers. VIrol J 7:355 (2010).

Lander GC, Tang L, Casjens SR, Gilcrease EB, Prevelige P, Poliakov A, Potter CS, Carragher B, and Johnson JE The structure of an infectious P22 virion shows the signal for headful DNA packaging. Science 312(5781):1791-95 (2006).

Frankel AD and Pabo, CO Cellular uptake of the tat protein from human immunodefiency virus Cell 55(6):1189-93 (1988).

Joliot A, Pernelle C, Deagostini-Bazin H, and Prochiantz A Antennapedia homeobox peptide regulates neural morphogenesis. Proc Natl Acad Sci U S A 88(5):1864-68.

Grimm D, Lee JS, Wang L, Desai T, Akache B, Storm TA, and Kay MA In vitro and in vivo gene therapy vector evolution via multispecies interbreeding and retargeting of adeno-associated viruses. J Virol 82(12):5887-911.

Steinman RM and Banchereau J Taking dendritic cells into medicine. Nature 449(7161):419-26 (2007).

Bonifaz LC, Bonnyay DP, Charalambous A, Darguste DI, Fujii S, Soares H, Brimnes MK, Moltedo B, Moran TM, and Steinman RM In vivo targeting of antigens to maturing dendritic cells via the DEC-205 receptor improves T cell vaccination. J Exp Med 199(6):815-24 (2004).

Jiang W, Swiggard WJ, Heufler C, Peng M, Mirza A, Steinman RM, and Nussenzweig MC The receptor DEC-205 expressed by dendritic cells and thymic epithelial cells is involved in antigen processing. Nature 375(6527):151-55.

van Kooten C and Banchereau J CD40-CD40 ligand J Leukoc Biol 67(1):2-17 (2000).

Akerstrom B, Brodin T, Reis K, and Bjorck L Protein G: a powerful tool for binding and detection of monoclonal and polyclonal antibodies. J Immunol 135(4):2589-92 (1985).

Shen Z, Reznikoff G, Dranoff G, and Rock KL Cloned dendritic cells can present exogenous antigens on both MHC class I and class II molecules. J Immunol 158(6):2723-30.

Jacobson RH, Zhang XJ, DuBose RF, and Matthews BW Three-dimensional structure of beta-galactosidase from E. coli. Nature 369(6483):761-66 (1994).

Asokan A, Schaffer DC, and Samulski RJ The AAV vector toolkit: poised at the clinical crossroads. Mol Ther 20(4):699-708 (2012).

Yang L, Yang H, Rideout K, Cho T, Joo KI, Ziegler L, Elliot A, Walls A, Yu D, Baltimore D, et al. Engineered lentivector targeting of dendritic cells for in vivo immunization. Nat Biotechnol 26(3):326-34 (2008).

Rappuoli R Bridging the knowledge gaps in vaccine design. Nat Biotechnol 25(12):1361-66 (2007).

Davtyan H, Mkrtichyan M, Movsesyan N, Petrushina I, Mamikonyan G, Cribbs DH, Agadjanyan MG, and Ghochikyan A DNA prime-protein boost increased the titer, avidity and persistence of anti-Abeta antibodies in wild-type mice. Gene Ther 17(2):261-71 (2009).

Smiley ST Immune defense against pneumonic plague. Immunol Rev 225:256-71 (2008).

Williamson ED Plague. Vaccine 27 Suppl 4:D56-60 (2009).

Do Y, Park CG, Kang YS, Park SH, Lynch RM, Lee H, Powell BS, and Steinman RM Broad T cell immunity to the LcrV virulence protein is induced by targeted delivery to DEC-205/CD205-positive mouse dendritic cells. Eur J Immunol 38 (1):20-29 (2008).

Carla MSR, and Virgil E Vaccine adjuvant methods and protocols ed. Davies G (Humana Press, New York), pp. 1-15 (2010).

Leuschner F, Dutta P, Gorbatov R, Novobrantseva TI, Donahoe JS, Courties G, Lee KM, Kim JI, Markmann JF, Marinelli B, et al. Therapeutic siRNA silencing in inflammatory monocytes in mice. Nat Biotechnol 29(11):1005-10 (2011).

Miki K, Uenaka H, Saito A, Miyagawa S, Sakaguchi T, Higuchi T, Shimizu T, Okano T, Yamanaka S, and Sawa Y Bioengineered myocardium derived from induced pluripotent stem cells improves cardiac function and attenuates cardiac remodeling following chronic myocardial infarction in rats. Stem Cells Transl Med 1(5)430-37 (2012).

Rossmann MG, Mesyanzhinov VV, Arisaka F, and Leiman PG The bacteriophage T4 DNA injection machines. Curr Opin Struct Biol 14(2):171-80 (2004).

Lata R, Conway JF, Cheng N, Duda RL, Hendrix TW, Wikoff WR, Johnson JE, Tsuruta H, and Steven AC Maturation dynamics of a viral capsid: visualization of transitional intermediate states. Cell 100(2):253-63 (2000).

Tao et al., In vitro and in vivo delivery of genes and proteins using bacteriophage T4 DNA packaging machine, PNAS, pp. 2-7.

Office Action received in related U.S. Appl. No. 14/337,545 to Rao et al., mailed Jan. 13, 2015.

de Wet et al., "Firefly Luciferase Gene: Structure and Expression in Mammalian Cells", Molecular and Cellular Biology, vol. 7, No. 2, pp. 725-737 (1987).

\* cited by examiner

FIG. 28

| Group # | F1-V | | Targeting molecular | Delivery system | Adjuvant |
|---|---|---|---|---|---|
| | DNA | Protein | | | |
| 1 | No | No | No | T4 head | None |
| 2 | No | Yes | No | None | Alum |
| 3 | No | Yes | No | T4 head | None |
| 4 | Yes | Yes | No | T4 head | None |
| 5 | Yes | Yes | DEC205mAb | T4 head | None |

FIG. 29

IN VITRO AND IN VIVO DELIVERY OF GENES AND PROTEINS USING THE BACTERIOPHAGE T4 DNA PACKAGING MACHINE

GOVERNMENT INTEREST STATEMENT

United States Government has rights in this invention pursuant to Contract No. NIAID U01-AI08086 and AI081726 awarded by National Institutes of Health.

CROSS-REFERENCE TO RELATED APPLICATIONS

This application claims benefit of priority to U.S. Provisional Patent Application No. 61/774,895 filed Mar. 8, 2013, entitled "In Vitro and In Vivo Delivery of Genes and Proteins Using the Bacteriophage T4 DNA Packaging Machine", which is incorporated by reference in its entirety.

This application also makes reference to the following U.S. patents and U.S. patent applications: U.S. Provisional Patent Application No. 60/904,168, filed Mar. 1, 2007, entitled "Liposome-Bacteriophage Complex as Vaccine Adjuvant"; U.S. patent application Ser. No. 12/039,803, filed Feb. 29, 2008, entitled "Liposome-Bacteriophage Complex as Vaccine Adjuvant", now U.S. Pat. No. 8,148,130, issued Apr. 3, 2012; U.S. patent application Ser. No. 11/015,294, filed Dec. 17, 2004, entitled "Methods and Compositions Comprising Bacteriophage Nanoparticles"; U.S. Provisional Patent Application No. 60/530,527, filed Dec. 17, 2003, entitled "Methods and Compositions Comprising Bacteriophage Nanoparticles"; U.S. Provisional Patent Application No. 61/322,334, filed Apr. 9, 2010, entitled "Promiscuous DNA Packaging Machine From Bacteriophage T4"; U.S. patent application Ser. No. 13/082,466, filed Apr. 8, 2011, entitled "Protein and Nucleic Acid Delivery Vehicles, Components and Mechanisms Thereof"; and U.S. Provisional Patent Application No. 61,731,147, filed Nov. 29, 2012, entitled "Designing a Soluble Full-Length HIV-1 GP41 Trimer", the entire contents and disclosures of which are incorporated herein by reference.

BACKGROUND

1. Field of the Invention

The present invention relates generally to protein and nucleic acid delivery components, compositions, mechanisms and methods of delivery thereof.

2. Related Art

Delivery of genes and proteins into target cells would be essential to generate mechanistic understanding as well as to explore novel biomedical therapies. For instance, future treatments of complex genetic and infectious diseases such as cancer and AIDS might include delivery of genes and proteins in appropriate combinations. Currently no platforms exist that can efficiently deliver both genes and proteins into target cells. The present application overcomes the shortcomings of the prior art as described herein.

SUMMARY

According to a first broad aspect, the present invention provides a method comprising the following steps: exposing cells of an individual to a T4 DNA packaging machine to thereby bind the T4 DNA packaging machine to the cells, wherein the T4 DNA packaging machine comprises one or more molecules of DNA packaged in the T4 DNA packaging machine, wherein there are one or more Soc-fused proteins displayed on the head, wherein there are one or more Hoc-fused proteins displayed on the head, and wherein step (a) causes internalization of the T4 DNA packaging machine within the cells, wherein internalization of the T4 DNA packaging machine within the cells causes the release of the packaged DNA into the cytosol of each of the cells, wherein the release of the packaged one or more molecules of DNA into the cytosol of each of the cells causes entry of the one or more molecules of DNA into the nucleus of each of the cells, wherein the entry of the one or more molecules of DNA into the nucleus of each of the cells causes transcription of the DNA and over-expression of protein(s) encoded by the DNA.

According to a second broad aspect, the present invention provides a method comprising the following step: exposing a head of a T4 DNA packaging machine to one or more Hoc-fused proteins to thereby display the one or more Hoc-fused proteins on the head, wherein packaged inside the T4 head is one or more DNA molecules, and wherein there are one or more Soc-fused proteins displayed on the head.

According to a third broad aspect, the present invention provides product comprising a T4 DNA packaging machine comprising: one or more DNA molecules packaged in a head of the T4 DNA packaging machine, one or more Hoc-fused proteins displayed on the head of the T4 DNA packaging machine, and one or more Soc-fused proteins displayed on the head of the T4 DNA packaging machine.

BRIEF DESCRIPTION OF THE DRAWINGS

The accompanying drawings, which are incorporated herein and constitute part of this specification, illustrate exemplary embodiments of the invention, and, together with the general description given above and the detailed description given below, serve to explain the features of the invention.

FIG. 28 is a flow chart illustrating the vaccination of five groups of mice by the intramuscular route with various formulations shown in FIG. 29.

FIG. 29 is a table summarizing the various formulations used to vaccinate five groups of mice by intramuscular route.

DETAILED DESCRIPTION OF THE PREFERRED EMBODIMENTS

Definitions

Figure 1:
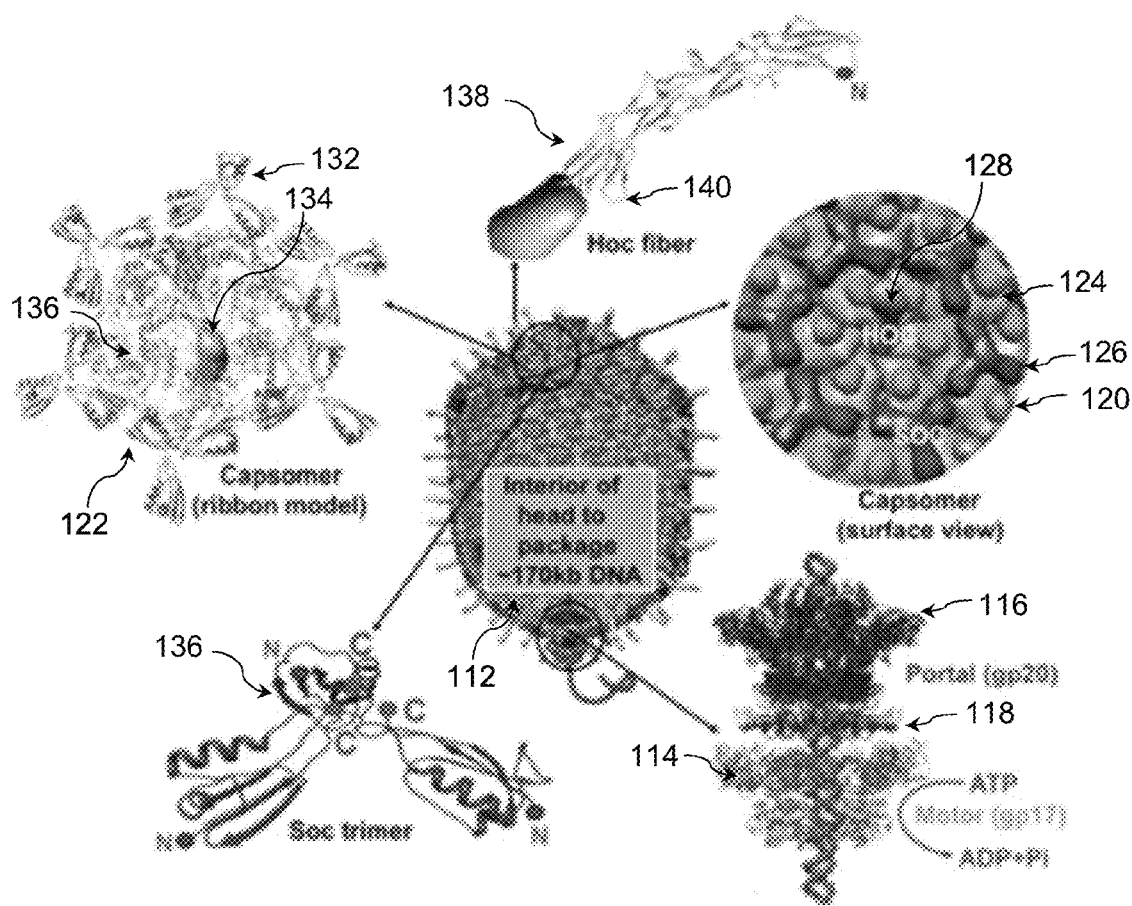
FIG. 1 is a schematic diagram of the bacteriophage T4 DNA packaging machine according to one embodiment of the present invention.

Where the definition of terms departs from the commonly used meaning of the term, applicant intends to utilize the definitions provided below, unless specifically indicated.

For purposes of the present invention, the term "bind," the term "binding" and the term "bound" refers to any type of chemical or physical binding, which includes but is not limited to covalent binding, hydrogen binding, electrostatic binding, biological tethers, transmembrane attachment, cell surface attachment and expression.

For purposes of the present invention, the term "biological sample" and the term "biological specimen" refers to either a part or the whole of a human, animal, microbe or plant in vitro or in vivo. The term includes but is not limited to material of human, animal, microbe or plant origin such as human, animal, microbial or plant tissue sections, cell or tissue cultures, suspension of human, animal, microbial or plant cells or isolated parts thereof, human or animal biopsies, blood samples, cell-containing fluids and secretion.

For purposes of the present invention, the term "capsid" and the term "capsid shell" refers to the protein shell of a virus comprising several structural subunits of proteins. The capsid encloses the nucleic acid core of the virus. The terms "prehead," "prohead" or "procapsid," "partial head" or "partially filled head," "full head" and "phage head" in singular or plural form, refer to different stages of maturity of the viral capsid shell. "Prehead" refers to a capsid shell of precise dimensions or an isometric capsid that is initially assembled, often with a single type of protein subunit polymerizing around a protein scaffold. When the protein scaffolding is removed, creating an empty space inside the capsid shell, the structure is referred to as a prohead or a procapsid. Partial head, full head and phage head all refer to capsids that reach a stage of maturation that makes them larger, more stable particles associated with DNA. The term "partial head" refers to a mature capsid shell that either has only a portion of DNA packaged into it or it may refer to a mature capsid shell that was once packed full with DNA and then the DNA releases from the shell to leave only a small portion of DNA behind. The term "full head" refers to a mature capsid shell that is fully packed with DNA. Full heads can pack up to 105% of the bacteriophage genome. This is about 165-170 kb for T4 bacteriophages. Similarly, capsids of other viruses can also be packaged to accommodate more than their genomic volume. The capsid may or may not be enveloped. The maturation process of capsids in bacteriophages like HK97 is described, for example, in Lata et al., 2000 (Reference 42).

For purposes of the present invention, the term "immune response" refers to a specific response of the immune system of an animal to antigen or immunogen. Immune response may include the production of antibodies and cellular immunity.

For purposes of the present invention, the term "immunity" refers to a state of resistance of a subject animal including a human to an infecting organism or substance. It will be understood that an infecting organism or substance is defined broadly and includes parasites, toxic substances, cancer cells and other cells as well as bacteria and viruses.

For purposes of the present invention, the term "immunization conditions" refers to factors that affect an immune response including the amount and kind of immunogen or adjuvant delivered to a subject animal including a human, method of delivery, number of inoculations, interval of inoculations, the type of subject animal and its condition. "Vaccine" refers to pharmaceutical formulations able to induce immunity.

For purposes of the present invention, the term "immunization dose" refers to the amount of antigen or immunogen needed to precipitate an immune response. This amount will vary with the presence and effectiveness of various adjuvants. This amount will vary with the animal and the antigen, immunogen and/or adjuvant but will generally be between about 0.1 µg/ml or less and about 100 µg per inoculation. The immunization dose is easily determined by methods well known to those skilled in the art, such as by conducting statistically valid host animal immunization and challenge studies.

For purposes of the present invention, the term "immunogen" and the term "immunogenic" refers to a substance or material (including antigens) that is able to induce an immune response alone or in conjunction with an adjuvant. Both natural and synthetic substances may be immunogens. An immunogen is generally a protein, peptide, polysaccharide, nucleoprotein, lipoprotein, synthetic polypeptide, or hapten linked to a protein, peptide, polysaccharide, nucleoprotein, lipoprotein or synthetic polypeptide or other bacterial, viral or protozoal fractions. It will be understood that "immunogen" or a composition that is "immunogenic" includes substances (e.g., small peptides) that do not generate an immune response (or generate only a therapeutically ineffective immune response) unless associated with an adjuvant. For purposes of the present invention, such immunogens are referred to as "adjuvant-obligatory" immunogens.

For purposes of the present invention, the term "individual" refers to a mammal. For example, the term "individual" may refer to a human individual.

For purposes of the present invention, the term "immunogenic amount" is an amount of an antigen preparation of interest or amount of a biological toxin that elicits a clinically detectable protective response in an animal.

For purposes of the present invention, the term "neck protein" and the term "tail protein" refers to proteins that are involved in the assembly of any part of the necks or tails of a virus particle, in particular bacteriophages. Tailed bacteriophages belong to the order Caudovirales and include three families: The Siphoviridae have long flexible tails and constitute the majority of the tailed viruses. Myoviridae have long rigid tails and are fully characterized by the tail sheath that contracts upon phage attachment to bacterial host. The smallest family of tailed viruses are podoviruses (phage with short, leg-like tails). For example, in T4 bacteriophage gp10 associates with gp11 to forms the tail pins of the baseplate. Tail-pin assembly is the first step of tail assembly. The tail of bacteriophage T4 consists of a contractile sheath surrounding a rigid tube and terminating in a multiprotein baseplate, to which the long and short tail fibers of the phage are attached. Once the heads are packaged with DNA, the proteins gp13, gp14 and gp15 assemble into a neck that seals of the packaged heads, with gp13 protein directly interacting with the portal protein gp20 following DNA packaging and gp14 and gp15 then assembling on the gp13 platform. Neck and tail proteins in T4 bacteriophage may include but are not limited to proteins gp6, gp25, gp53, gp8, gp10, gp11, gp7, gp29, gp27, gp5, gp28, gp12, gp9, gp48, gp54, gp3, gp18, gp19, gp13, gp14, gp15 and gp63. Aspects of the neck and tail assembly proteins in T4 bacteriophage and other viruses are described further, for example, in Rossmann et al., 2004 (Reference 41).

For purposes of the present invention, the term "non-naturally occurring" or "isolated" refers to the component of interest being at least substantially free from at least one other component with which it is naturally associated in nature and as found in nature.

For purposes of the present invention, the term "packaging machine" refers to the complete packaging unit including the compartment, the motor and the component or any other attachment mechanism that connects the motor to the compartment. For example, the T4 packaging machine comprises the shell (the procapsid made primarily of gp23), the vertex portal protein (dodecameric gp20) and the gp17 packaging motor. The T4 DNA packaging machine is further described, for example, in Zhang et al., 2011.

For purposes of the present invention, the term "packaging motor" refers to a molecular motor or a molecular machine that is capable of using chemical energy to drive the mechanical translocation of a nucleic acid and package the nucleic acid into a compartment. For example, the packaging motor in T4 bacteriophage uses the energy of ATP hydrolysis to translocate and package DNA into the capsid shell. The packaging motor may be a protein complex comprising one or more protein subunits and have enzymatic activities that help package nucleic acids, which include, but are not limited to ATPase, nuclease and translocase. For example, T4 bacteriophage packaging motor refers to a large terminase protein, the pentameric gene product (gp)17. The term "packaging motor" may also be considered to encompass additional proteins that regulate or enhance the activity of the actual motor. For example, the T4 packaging motor may also include a small terminase protein gp16. The T4 DNA packaging motor is further described in, for example, Sun et al., 2008.

For purposes of the present invention, the term "peptide-like" refers to short chain peptides as well as proteins, lipoproteins and glycoproteins, but will also, for convenience, include non-proteinaceous molecules, for example, amino acid-containing molecules. In certain embodiments, the peptide-like therapeutic agent may additionally comprise vitamins, steroids, azidothymidine, and free primaquine in addition to other agents. One useful class of peptides is immunomodulators such as interleukins, colony stimulating factors and interferons. Another useful class of proteins is antigens and immunogens such as are used in vaccines.

For purposes of the present invention, the term "purified" refers to the component in a relatively pure state—e.g. at least about 90% pure, or at least about 95% pure or at least about 98% pure.

For purposes of the present invention, the term "targeting ligand" refers to proteins or receptors displayed on the surface of cells like dendritic cells and antigen-presenting cells. The binding of a targeting ligand to an antigen-presenting or dendritic cell is required for cellular activation and induction of a variety of downstream effects.

For purposes of the present invention, the term "targeting molecule" refers to a naturally existing cellular or molecular structure involved in the pathology of interest that the drug-in-development is meant to act on.

For purposes of the present invention, the term "virus particle" refers to viruses and virus-like organisms.

Description

Delivery of recombinant genes and proteins into cells forms the core of molecular biology and biotechnology. While numerous methods have been developed to deliver genes; electroporation (Neumann et al., 2011 (Reference 1)), viral vectors (Kay, 2011 (Reference 2)), and microinjection (Demayo et al., 2012 (Reference 3)) to name a few, protein delivery is less common (Yan et al., 2010; Kaczmarczyk et al., 2011 (References 4 and 5)). But no platforms currently exist that can efficiently deliver both genes and proteins. With the explosion of genomics and protein network databases, delivery of genes and proteins into target cells would be essential to generate mechanistic understanding as well as to explore novel biomedical therapies. For instance, future treatments of complex genetic and infectious diseases such as cancer and AIDS might include delivery of genes and proteins in appropriate combinations, which is referred to herein as "progene delivery."

In one embodiment, the present invention provides customized bacteriophages uniquely designed for effective delivery of mammalian genes and proteins into target cells. The methods and compositions of the present invention may be used for effective vaccine and genetic therapies.

In one embodiment, the present invention uses the phage T4 DNA packaging machine to provide a high capacity progene delivery vehicle. Tailed phages employ powerful molecular machines to condense the highly negatively charged DNA genome inside a capsid to near crystalline density (>500 mg/ml). These machines generate forces as high as 80 pN in order to oppose the electrostatic repulsion and bending energies that resist DNA compaction (Smith et al., 2001 (Reference 6)). The phage T4 packaging machine, one of the fastest (packaging rate up to ~2000 bp/sec) and most powerful (power density, ~5000 kW/m$^3$) (Fuller et al., 2007 (Reference 7)) packaging machines, consists of two essential components; an empty prohead and a molecular motor comprised of five subunits of the large terminase protein, gp17 (Casjens, 2011 (Reference 8); Rao et al., 2008 (Reference 9); Sun et al., 2008 (Reference 10)) (FIG. 1). In FIG. 1, 112 is a structural model of the phage T4 packaging machine showing pentameric motor 114 assembled at the dodecameric portal vertex 116, in ribbon model 118 (Sun et al., 2004 (Reference 10); Fokine et al., 2004 (Reference 11)).

As shown in FIG. 1, phage T4 head capsomer (surface view 120; ribbon model 122) is decorated with two outer capsid proteins, Hoc (highly antigenic outer capsid protein; 155 copies/head) and Soc (small outer capsid protein; 870 copies/head) (Fokine et al., 2004 (Reference 11)). Surface view 120 of the capsomer shows the arrangement of major capsid protein gp23 124, Soc trimers 126 and Hoc fiber 128. Ribbon model of capsomer 122 shows ribbon models of gp23 130, Soc 132 and Hoc 134. The nanomolar affinity binding sites for Hoc and Soc appear after the prohead has undergone "expansion", a major conformational change in the capsid protein, gp23 (Black et al., 1994 (Reference 12)). The tadpole shaped Soc (9 kDa) assembles as a trimer at the quasi three-fold axes, champing the adjacent capsomers and forming a reinforcing cage around the shell (Qin et al., 2010 (Reference 13)) (see 120, 122 and Soc trimer ribbon model 136. Soc trimer ribbon model 136 shows exposed N- and C-termini (Qin et al., 2010 (Reference 13)). About 180 Å-long linear fibers of Hoc (41 kDa), each having a string of four domains three of which IgG-like, assemble at the center of hexameric capsomers (Fokine et al., 2011 (Reference 14)) (see 120, 122 and Hoc fiber 138. Hoc fiber 138 shows the exposed N-terminus at the tip of the fiber (Fokine et al., 2011 (Reference 14)). The C-terminal Hoc domain 4 binds to capsid but its structure has not yet been solved, hence shown as mass 140 at the base of the fiber. Hoc facilitates attachment of phage to bacteria. Soc and Hoc are not essential for phage infection but provide survival advantages for the virus (Ishii et al., 1977 (Reference 15)). The N- and C-termini of Soc, as shown by 136 and 138, are well exposed allowing efficient display of foreign proteins on the capsid surface (Li et al., 2006 (Reference 16); Sathaliyawala et al., 2006 (Reference 17)).

Recently, a neck-less (13am), tail-less (10am) hoc and soc deletion mutant that accumulates packaged heads was constructed (Zhang et al, 2011 (Reference 18)). In the classic assembly pathway, the packaging motor assembles on a prohead and after head maturation and (headful) genome packaging, the motor dissociates. Then the neck proteins, gp16, gp14, and gp15, attach to the portal sealing off the packaged head. Tail and tail fibers attach to the neck producing an infectious virion (Leiman et al., 2010 (Reference 19)). In the neck-less mutant, the packaged heads become unstable and release the DNA due to internal pressure, which is estimated to be ~6 MPa or >10-times the pressure in a champagne bottle (Smith et al., 2001 (Reference 6); Lander et al., 2006 (Reference 20)). Unexpectedly, it was discovered that the packaging motor can re-assemble on this fully matured, emptied phage head and re-fill with any DNA (Zhang et al., 2011 (Reference 18)). The T4 packaging machine, thus, is promiscuous, neither discriminating the head on which it assemble nor the DNA that it packages.

These findings raised the question of whether the phage packaging machine could be re-configured to deliver genes and proteins into mammalian cells. Conceivably, each head could package several genes inside, up to ~170 kb, and display several proteins outside, up to ~1,025 molecules, and deliver the entire "payload" into cells. Such a system would be attractive not only because of its large capacity but also that T4 is noninfectious, nontoxic, and has no pre-existing immunity. Disclosed embodiments herein show that combinations of reporter genes, vaccine genes, functional enzymes and targeting ligands can be incorporated into the T4 head and delivered into mammalian cells to near 100% efficiency. Disclosed embodiments further demonstrate that delivery can be targeted to antigen presenting dendritic both in vitro and in vivo. Mice immunized with a single dose of "prime-boost" plague vaccine containing the recombinant F1-V gene from *Yersinia pestis* packaged inside the T4 head and the F1-V protein displayed outside elicited robust antibody and cellular immune responses, thus establishing for the first time, a unique phage-based mammalian gene and protein delivery system that could lead to novel vaccine and genetic therapies.

Figure 2:
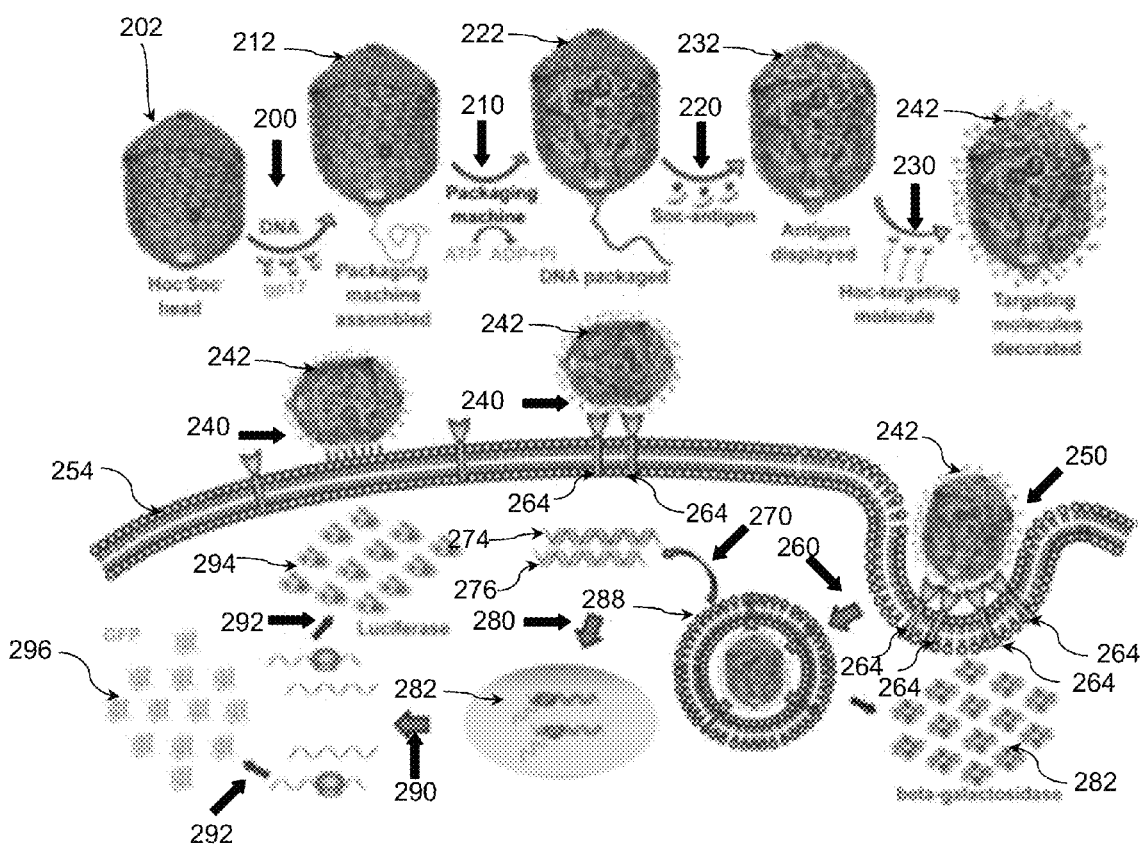
FIG. 2 is a schematic illustrating the experimental design for progene delivery according to one embodiment of the present invention.

In a preferred embodiment, a detailed experimental scheme was developed to quantitatively analyze progene delivery by T4. In step 200, the T4 DNA packaging machine was first assembled by binding the gp17 subunits at the dodecameric portal (gp20) of empty phage head 202, as shown in FIG. 2. In step 210, fueled by ATP, the machine packages DNA into head 212, up to ~170 kb, to produce head 214. In step 220, Soc-fused proteins were added and displayed on capsid surface, as shown in 222. In step 230, Hoc-fused proteins were added to decorate the capsid surface, as shown in 232. Head particle 232 then binds to cell 234 either nonspecifically (general delivery, step 240) or through host receptors 244 (targeted delivery, step 250) and are internalized (step 260). Surface displayed protein like β-galactosidase 262 and encapsulated DNA, namely DNA 264 including luciferase gene 264 and DNA 266 including green fluorescent protein (GFP) gene are released into cytosol 268 in step 270. DNA 264 and 266 enter nucleus 272 in step 280, priming transcription (282) under strong CMV promoter (not shown) and over-expression (284) of luciferase (286) and GFP (288) proteins.

The T4 Progene Particles are Efficiently Assembled In Vitro

Figure 3:
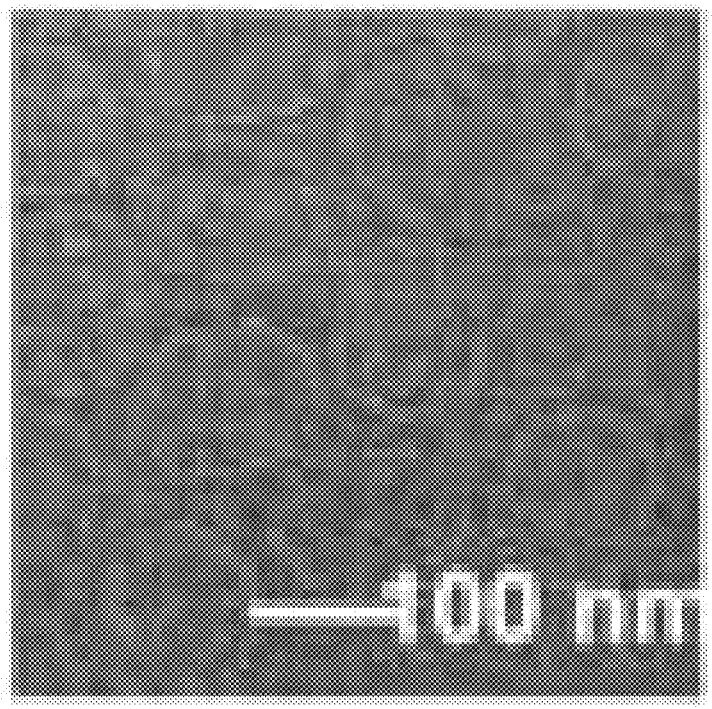
FIG. 3 is a cryo-electron micrograph of purified T4 heads according to one embodiment of the present invention.
Figure 4:
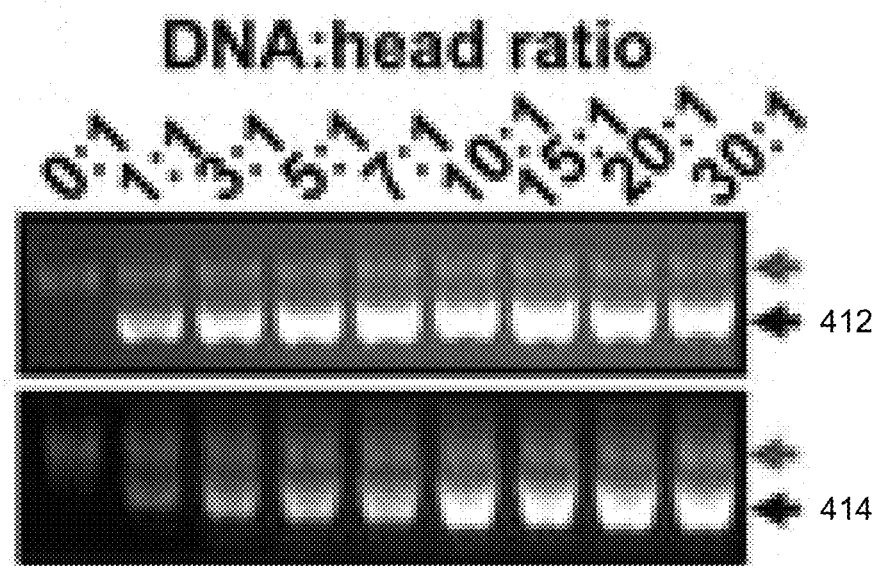
FIG. 4 is a micrograph showing packaging of MluI-linearized pEGFP-C1 plasmid DNA (top panel) and BamHI-linearized psiCHECK2 plasmid DNA (bottom panel) into Hoc⁻ Soc⁻ T4 heads at increasing DNA to ratios. Arrows 412 and 414 show the packaged DNA according to one embodiment of the present invention.
Figure 5:
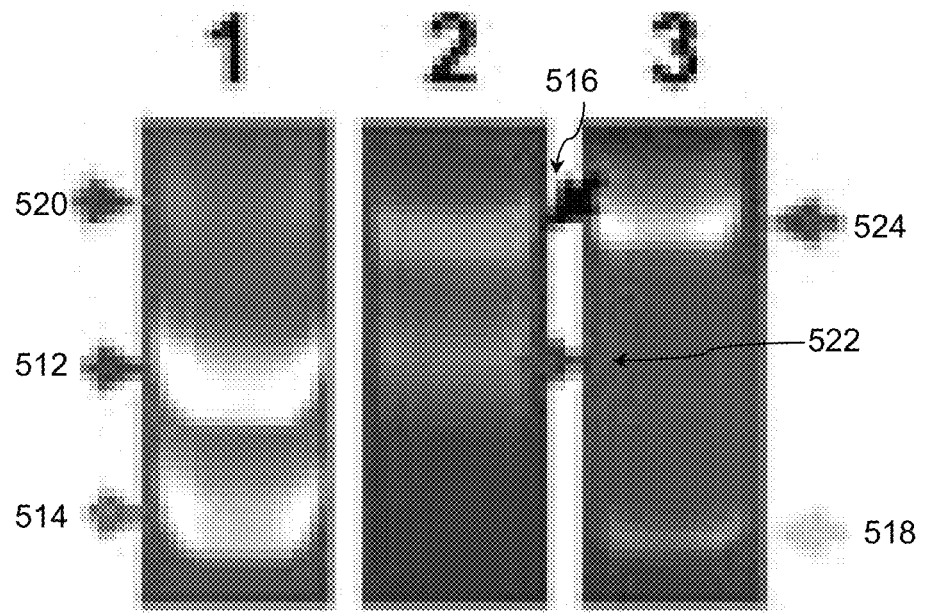
FIG. 5 is a micrograph showing packaging of two plasmids, concatemerized luciferase DNA and PCR amplified luciferase expression cassette according to one embodiment of the present invention.
Figure 6:
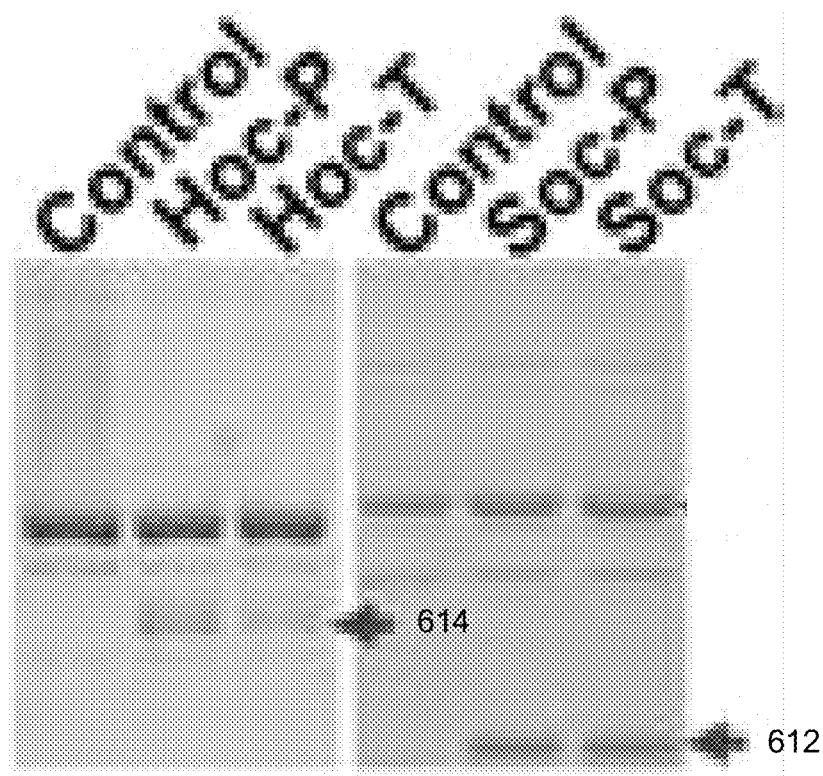
FIG. 6 is a micrograph showing in vitro assembly of cell penetration peptides (CPPs) on T4 heads according to one embodiment of the present invention.
Figure 7:
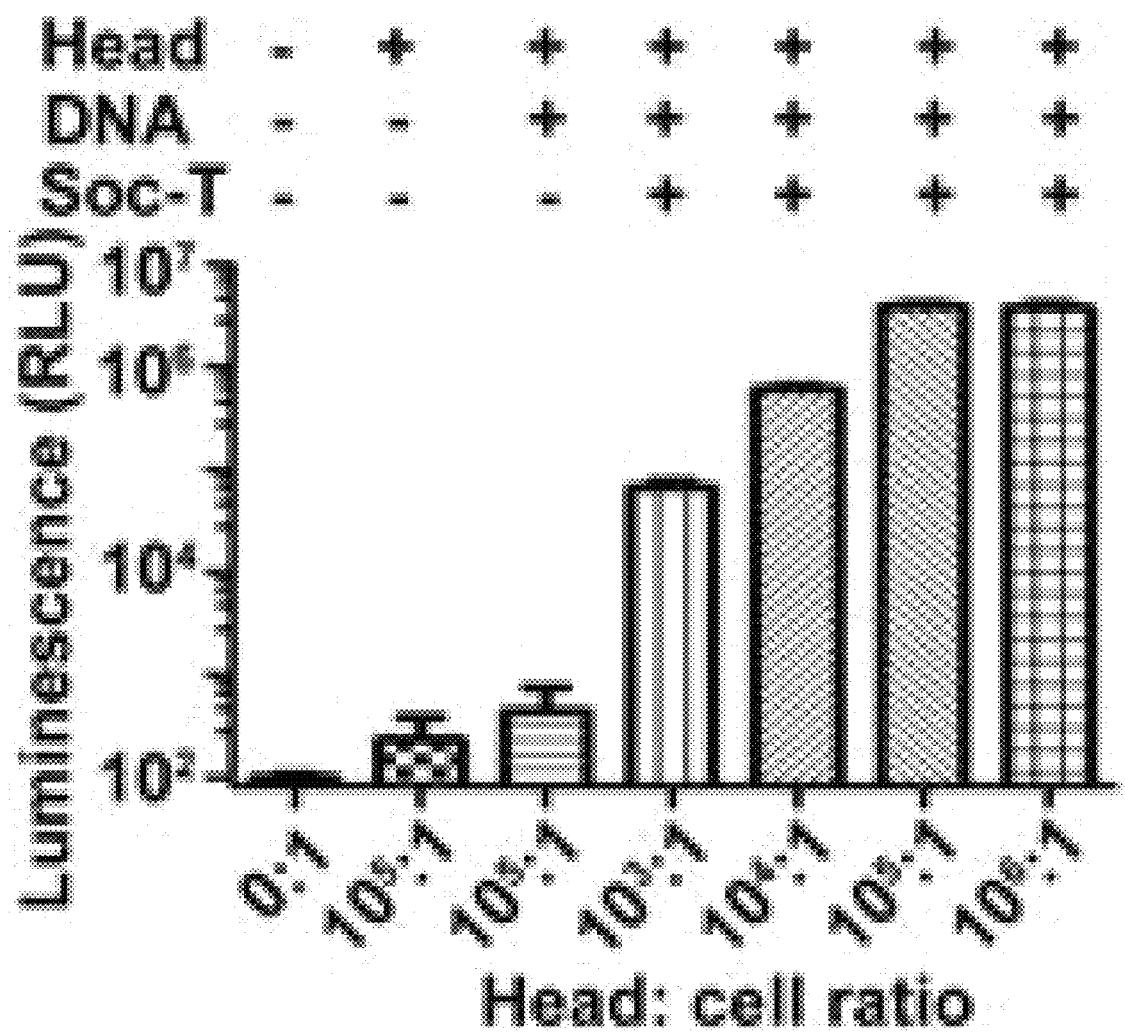
FIG. 7 is a graph showing dose-dependent delivery of luciferase DNA into mammalian cells using CPP-decorated T4 heads according to one embodiment of the present invention.
Figure 8:
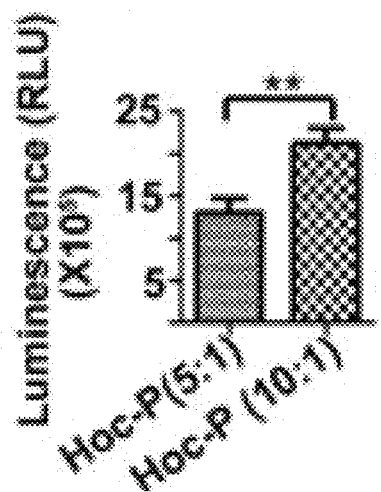
FIG. 8 is a graph illustrating how luciferase DNA delivery increases with increasing copy number of CPP.

According to another embodiment, the neck-less heads from *E. coli* cells infected with 10am103amhoc$^-$soc$^-$ mutant were first isolated, as seen in FIG. 3. Most of these heads, ~90%, released the viral genome spontaneously, which was digested with DNase I. The emptied heads retained a ~8-kb DNA inside, the leaving the rest of the ~162-kb space available for foreign DNA. The heads were purified by CsCl gradient centrifugation and ion-exchange chromatography and mixed with gp17 to reconstitute the functional packaging machines. These machines re-filled the heads at high efficiency as shown by bulk and single molecule assays. CryoEM indicated that most of the machines actively encapsidated DNA. Single (FIG. 4) or multiple plasmids, long ~80 kb ligated DNA (up to ~170 kb) or short 2.3 kb PCR-amplified DNA (FIG. 5) were efficiently packaged. Along lane 1 in FIG. 5, luciferase is indicated by arrow 512 while eGFP is indicated by arrow 514. In lane 2, concatemerized DNA is indicated by arrow 516 and PCR amplified luciferase expression cassette in lane 3 is indicated by arrow 518. Arrows 520, 522 and 524 show the 8 kb T4 DNA present in the heads. On average, up to ten molecules of plasmid DNA were packaged per head when the DNA to head ratio was ~30:1, as depicted in FIG. 4. When two (or more) plasmid DNAs were present, both packaged, at roughly equal frequencies (FIG. 5, lane 1). Foreign peptides (cell penetration peptides; CPPs) and proteins (β-galactosidase, DEC205mAb, CD40 ligand etc.) were then arrayed on the surface by adding the Soc- and Hoc-fused recombinants to the reaction mixture (FIG. 6). In FIG. 6, arrow 612 shows bound Soc-T and Soc-P and arrow 614 shows bound Hoc-T and Hoc-P; control lanes show purified heads. Soc and Hoc binding to capsid followed simple first order by varying the ratio of Soc- or Hoc-fusion protein molecules to binding sites (FIGS. 6 and 7). At a ratio of 20:1, nearly all the capsid binding sites were occupied.

Engineered T4 Particles Efficiently Delivered Genes into Mammalian Cells

Initial experiments in this present invention showed that T4 delivery of luciferase gene into HEK293T cells was very poor. However, when the particles were decorated with CPP-Tat (CPP-T) or CPP-Antp (CPP-P) (FIG. 6), delivery was efficient, as shown by the appearance of high luciferase activity in the cell lysates (FIGS. 7, 8, 9 and 10). CPPs are 20-30 amino acid peptides rich in basic amino acids that facilitate passage of attached cargo molecules across the cell membrane. Tat and Antp refer to CPPs of HIV-1 trans-activator protein drosophila antennapedia homeobox protein, respectively (Frankel et al., 1988 (Reference 21); Joliot et al., 1991 (Reference 22)). Luciferase activity reached the maximum at $10^5$ heads per cell (FIG. 7). The activity appeared by as early as 5 hours, reaching a peak by about 16 hours and was sustained for at least 30 hours.

Figure 9:
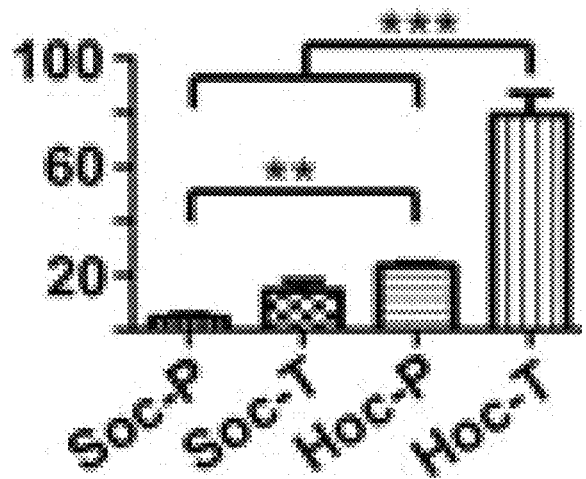
FIG. 9 is a graph showing how Hoc-CPP decorated heads deliver genes more efficiently than Soc-CPP heads.
Figure 10:
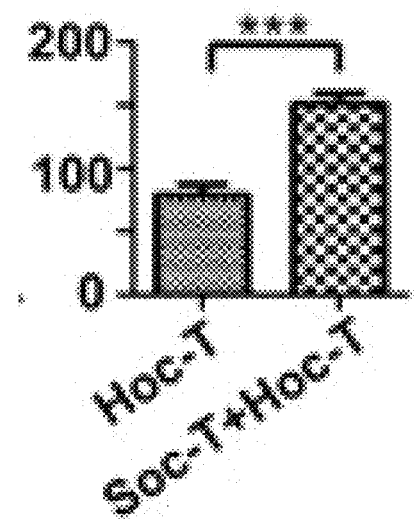
FIG. 10 is a graph showing that gene delivery was at its highest when the heads were decorated with both Hoc-T and Soc-T CPPs according to one embodiment of the present invention.
Figure 11:
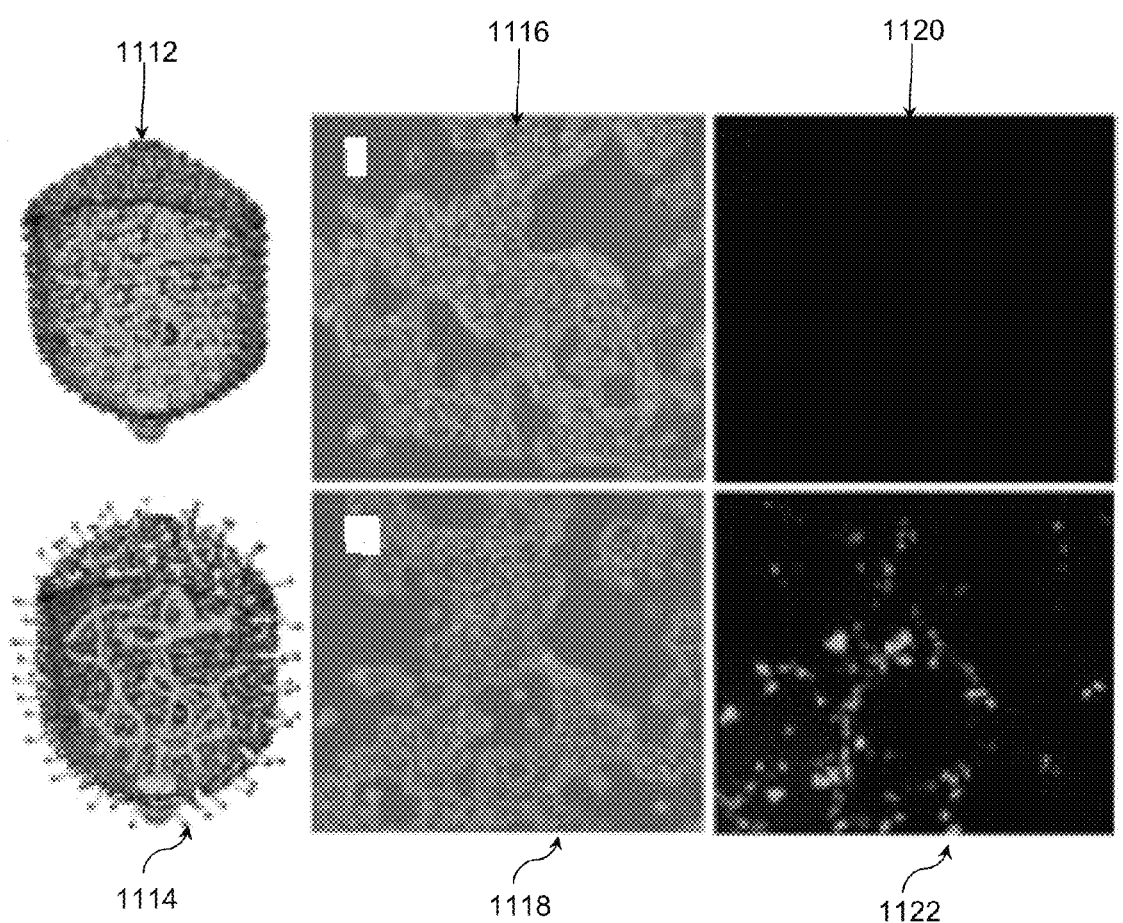
FIG. 11 is a series of micrographs showing eGFP DNA packaged heads decorated with or without Hoc-CPPs for delivery, as well as HEK293T cells in the presence/absence of CPP.
Figure 12:
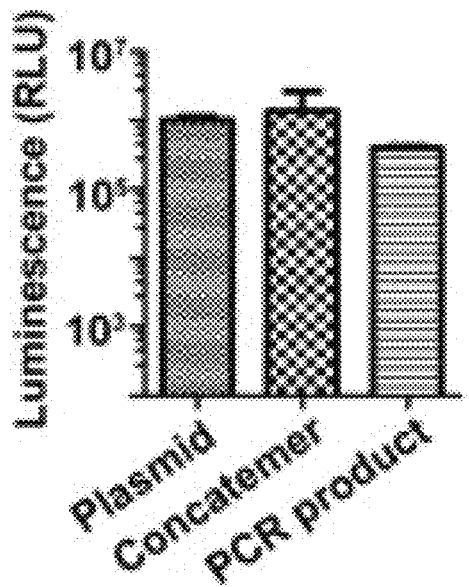
FIG. 12 is a graph illustrating expression of packaged and delivered luciferase gene as plasmid, concatemer, or PCR product.

Luciferase activity increased with increasing copy number of CPP (FIG. 8) but at a given copy number, CPP-T is 3.3-fold more effective than CPP-P (FIG. 9). This is presumably because the Hoc-fused CPP is positioned ~180 Å away from capsid surface (height of Hoc fiber), thus having greater reach to contact the cell membrane of the mammalian cell when compared to Soc-CPP that is nearly glued to the capsid wall (Qin et al. (Reference 13), 2010; Fokine et al., 2011 (Reference 14)) (FIG. 1). Combining Hoc-CPP and Soc-CPP further increased delivery efficiency by 1.9-fold (FIG. 10). The delivery efficiency was roughly the same whether the packaged DNA was a plasmid, short PCR-amplified DNA, or ligated into a long concatemer (FIG. 12). Parallel experiments using another plasmid, pEGFP-C1, gave similar results with nearly 100% of cells showing green fluorescence (FIG. 11). In FIG. 11, eGFP DNA packaged heads that are either decorated without Hoc-CPPs (panel 1112) or with Hoc-CPPs (panel 1114) are used for delivery. Panels 1116 and 1118 are phase contrast micrographs of HEK293T cells—panel 1116 in the absence of CPP; panel 1118 in the presence of CPP. Panes 1120 and 1122 are fluorescence micrographs of HEK293T cells—panel 1120 in the absence of CPP; panel 1122 in the presence of CPP.

Proheads or isometric phage heads can also be used as delivery vehicles but the fully mature emptied phage heads, which are extremely stable and can be produced in large quantities (~$5 \times 10^{13}$ particles per liter culture) were the heads of choice. Preliminary experiments using inhibitors indicated that the T4 head delivery was mediated by an endocytic pathway that is energy-dependent and require actin polymerization but not clathrin or caveolin. No significant toxicity was observed following T4 delivery, even up to a ratio of $10^6$ head particles per cell.

Figure 13:
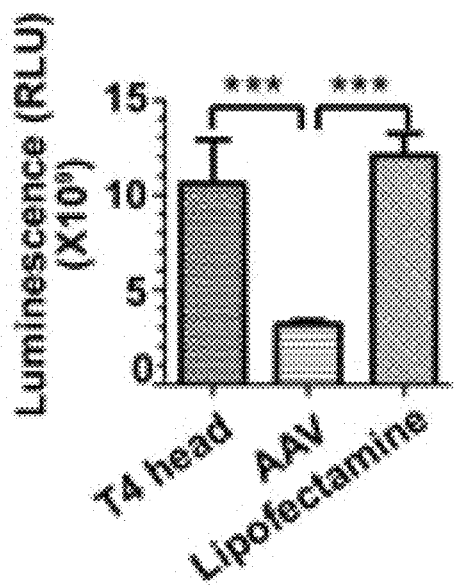
FIG. 13 is a graph drawing comparison of the delivery efficiencies of T4, AAV-DJ and lipofectamine.

The T4 delivery efficiency was assessed to be very high, approaching as many as $10^5$ luminescence units per cell (FIG. 13). To determine how this efficiency compared to lipofectamine and AAV, the two most efficient transfection systems currently available, luciferase gene was delivered into HEK293T cells under conditions that are optimal for each of these systems. The data showed that the T4 efficiency was similar to that of the lipofectamine but ~3.3-times higher than that of the AAV-DJ vector, the most efficient AAV vector reported to date (Grimm et al., 2008, (Reference 23)) (FIG. 13).

Targeted Delivery of Genes and Proteins into Dendritic Cells by T4

Figure 14:
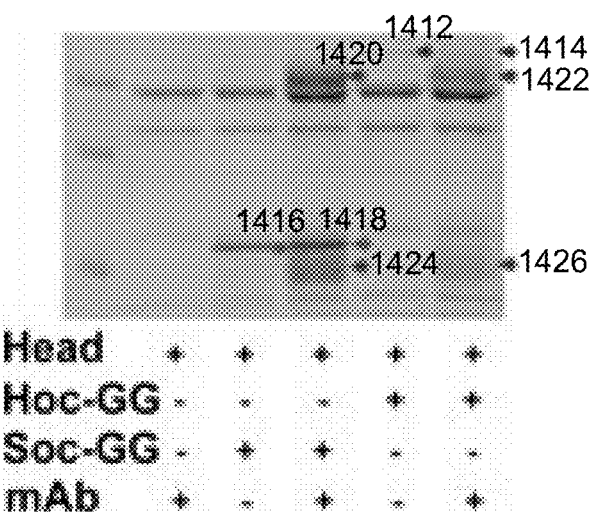
FIG. 14 is a micrograph that shows display of DEC205mAb on T4 heads through GG domain.
Figure 15:
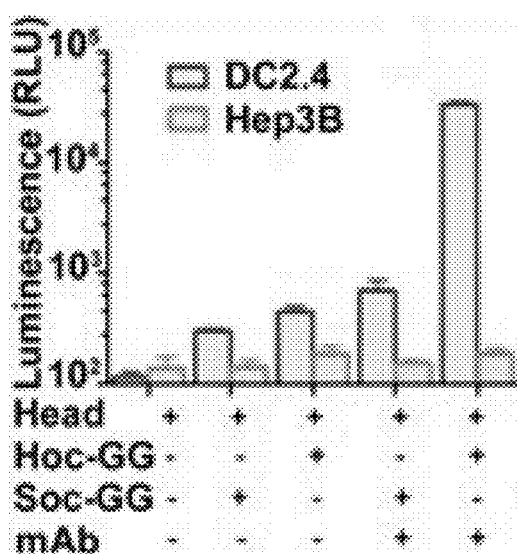
FIG. 15 is a graph showing targeted delivery of luciferase gene into DC2.4 cells but not into control Hep3B cells.
Figure 16:
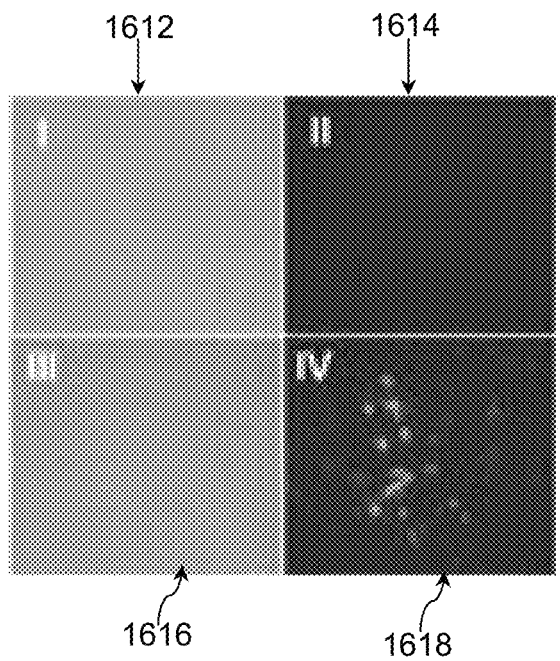
FIG. 16 is a series of phase contrast and fluorescence micrographs of DC2.4 cells transduced with green fluorescent protein (GFP) heads in the presence or absence of displayed DEC205mAb.
Figure 19:
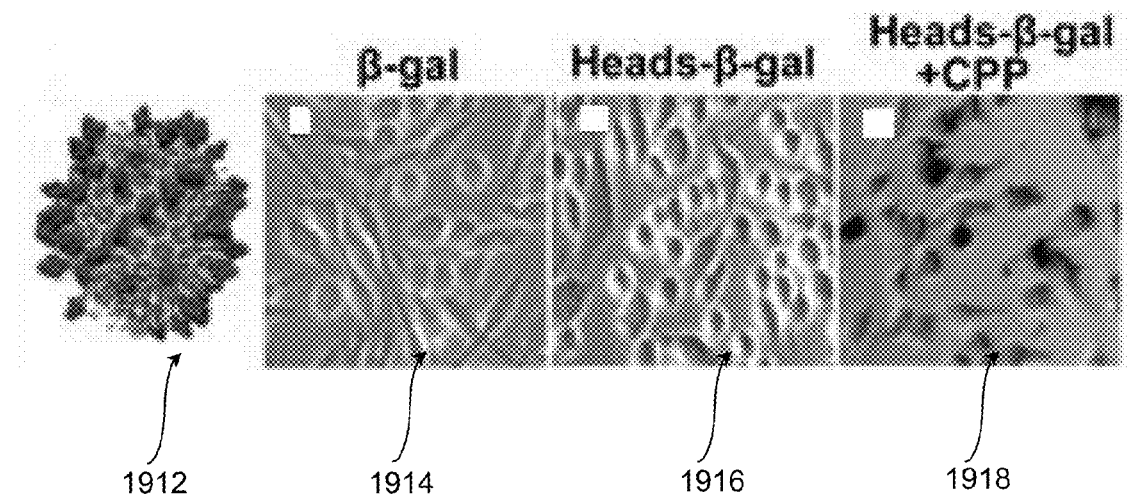
FIG. 19 is a series of micrographs of T4 heads displayed with β-galactosidase and CPP delivering functional β-galactosidase into DC2.4 cells.

The antigen presenting dendritic cells were chosen to test if T4 delivery can be targeted to specific cells. Dendritic cells are critical for vaccine uptake and induction of humoral as well as cellular immune responses (Steinman et al., 2007 (Reference 24)). The hypothesis in disclosed embodiments of this present invention is that displaying a dendritic cell-specific ligand on the capsid lattice would enable T4 to capture dendritic cells leading to endocytosis and delivery of the attached cargo. To test this hypothesis, the DEC205mAb of the CD40 ligand (CD40L) which recognized the dendritic cell-specific DEC205 receptor (Bonifaz et al., 2004 (Reference 25); Jiang et al., 1995 (Reference 26)) and CD40 (Reference 27) respectively, were displayed on the T4 heads. The heads were first packaged with luciferase and/or eGFP genes and incubated with the Hoc-GG fusion protein plus DEC205mAb. The GG fusion contained two tandemly-linked 122-amino acid IgG binding domains of protein G (Akerstrom et al., 1985 (Reference 28)) from *Streptomyces* which when attached to T4 head through Hoc captured the Fc region and formed arrays of DEC205mAb on the head with their receptor binding Fab regions well exposed (FIGS. 14 and 19). In FIG. 14, Hoc-GG, Soc-GG and DEC205mAb bands are marked with arrows 1412 and 1414 (Hoc-GG), 1416 and 1418 (Soc-GG), DEC205mAb (1420, 1422, 1424 and 1426). These particles efficiently delivered the packaged luciferase gene into mouse DC2.4 cells (Shen et al., 1997 (Reference 29)) but were unable to do so into nonspecific cells such as Hep3B cells that lacked the receptor (FIG. 15). Delivery efficiency was nearly 100% in several independent experiments (FIG. 16). In FIG. 16, 1612 and 1614 are phase contrast and fluorescence micrographs of DC2.4 cells transduced with GFP heads in the absence of displayed DEC205mAb, respectively. 1616 and 1618 are phase contrast and fluorescence micrographs of DC2.4 cells transduced with GFP heads in the presence of displayed DEC205mAb, respectively. When both the luciferase and eGFP genes were packaged into the same head, the heads delivered both the gene to near 100% efficiency as shown by the presence of both the luciferase and green fluorescence signals in the HEK293T cells but not in the control cells. Similar results were also obtained using the displayed CD40L fused to the N-terminus of Hoc.

Figure 17:
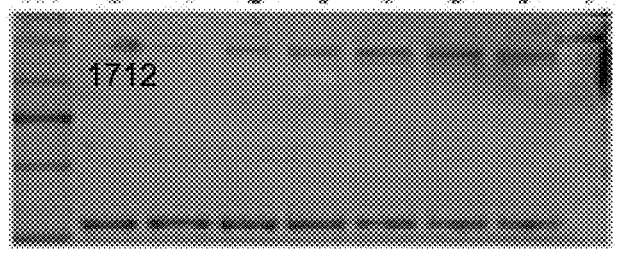
FIG. 17 is a micrograph displaying tetrameric β-galactosidase on T4 heads at different rations of β-galactosidase-Soc molecules to Soc binding sites.
Figure 18:
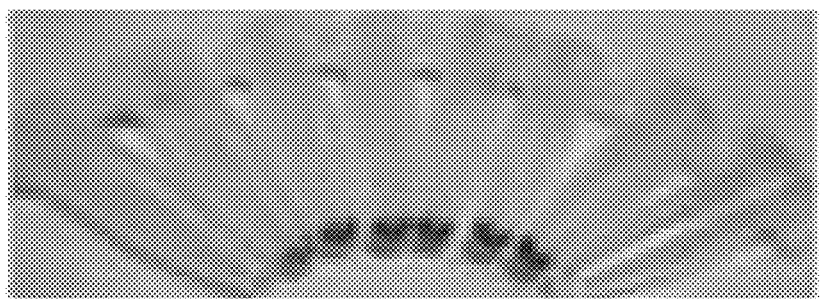
FIG. 18 is a micrograph showing of X-gal cleavage activity of displayed β-galactosidase corresponding to lanes in FIG. 17.
Figure 20:
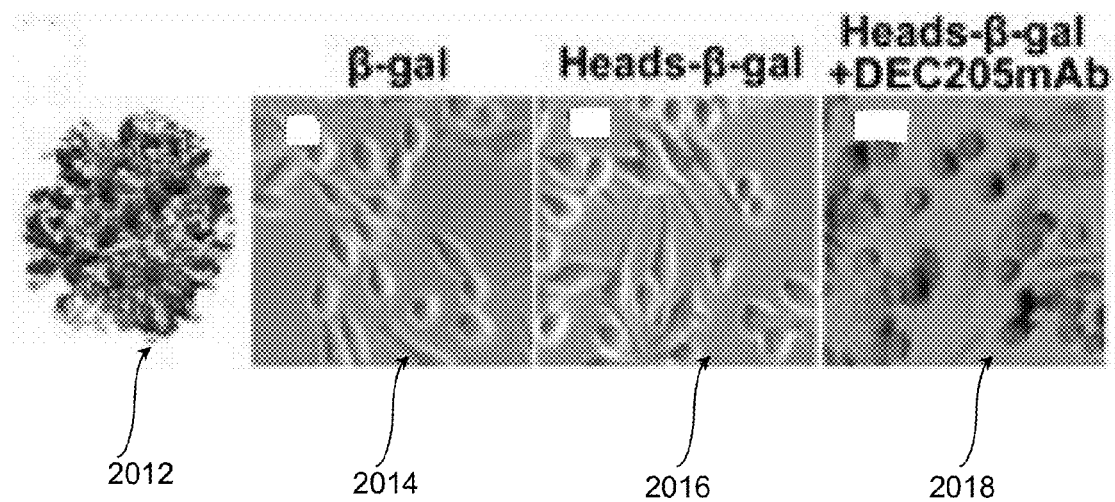
FIG. 20 is a series of micrographs of T4 heads displayed with β-galactosidase and DEC205mAb delivering functional β-galactosidase into DC2.4 cells.

Disclosed embodiments also tested protein delivery into dendritic cells using the 159 kDa *E. coli* β-galactosidase as the model protein. This is a stringent test because β-galactosidase is functional only as a tetramer (Jacobson et al., 1994 (Reference 30)). Hence the Soc-fused protein must oligomerize into a >500 kDa complex and be efficiently displayed on T4 heads (FIG. 17) and the resultant heads showed β-galactosidase activity (FIG. 18). Arrow 1712 in FIG. 17 shows bound β-galactosidase-Soc, and the 40:0 lane is the control lane showing no nonspecific binding of β-galactosidase-Soc in the absence of heads. Hoc-fused CPP-T or DEC205mAb was then decorated on the same heads (FIGS. 19 and 20; panels 1912 and 2012). These heads when incubated with dendritic cells showed delivery of β-galactosidase into nearly 100% of the cells, as shown by the appearance of blue X-gal (FIGS. 19 and 20; panels 1918 and 2018). Control particles containing either no targeting ligand (FIGS. 19 and 20; panels 1916 and 2016), or the soluble enzyme alone (FIGS. 19 and 20; panels 1914 and 2014), showed poor to no signal.

Figure 21:
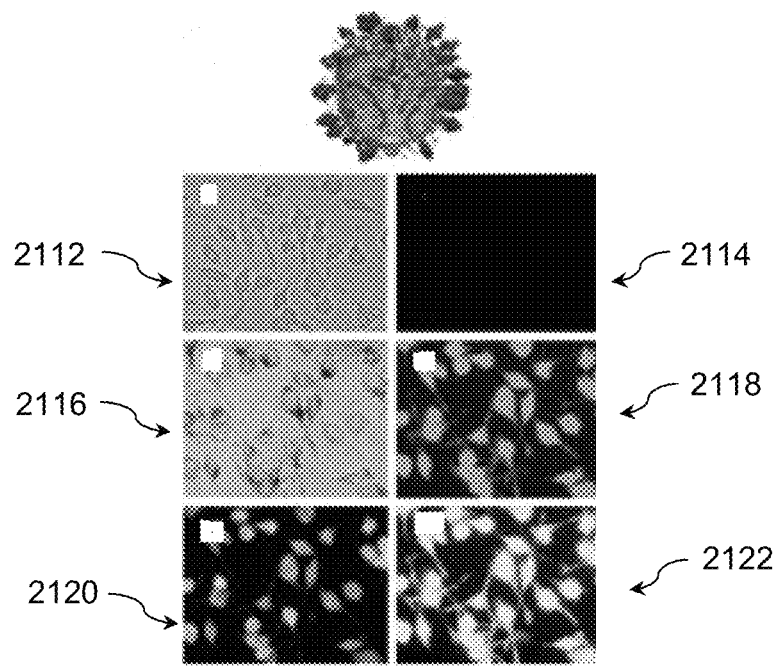
FIG. 21 is a series of micrographs of T4 heads packaged inside with luciferase and GFP DNA and displayed outside with β-galactosidase and CPP used for delivery.
Figure 22:
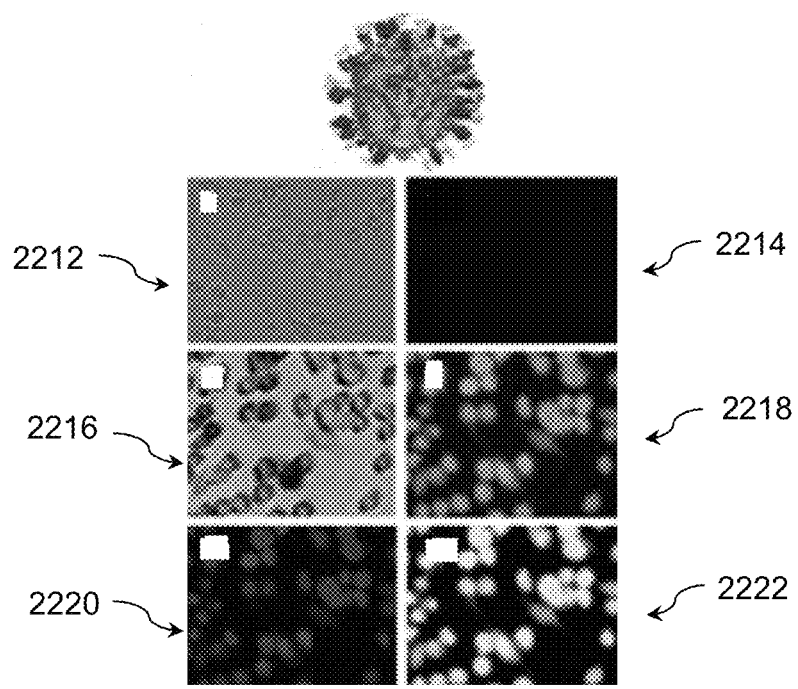
FIG. 22 is a series of micrographs of T4 heads packaged inside with luciferase and GFP DNA and displayed outside with β-galactosidase and DEC205mAb used for delivery.

To ascertain if T4 can simultaneously deliver both genes and proteins into cells, the heads were first packaged with luciferase and eGFP plasmids and the surface was decorated with β-galactosidase as Soc fusion, and CPP (FIG. 21) or DEC205mAb (FIG. 22). as Hoc fusion, and tested if the entire payload could be delivered into dendritic cells. In FIG. 21, panel 2112 shows a phase contrast micrograph of DC2.4 cells transduced with control packaged heads containing no CPP, panel 2114 shows a fluorescence micrograph of DC2.4 cells transduced with control packaged heads containing no CPP, panel 2116 shows DC2.4 cells stained for β-galactosidase activity with X-gal, panel 2118 is fluorescence image of eGFP after staining with FITC-labeled antibody, panel 2120 is a fluorescence image of luciferase after staining with Rhodamine-labeled antibody and panel 2122 is a merged fluorescence image of eGFP and luciferase. In FIG. 22, panel 2212 shows a phase contrast micrograph of DC2.4 cells transduced with control packaged heads containing no DEC205mAb, panel 2214 shows a fluorescence micrograph of DC2.4 cells transduced with control packaged heads containing no DEC205mAb, panel 2216 shows DC2.4 cells stained for β-galactosidase activity with X-gal, panel 2218 is a fluorescence image of eGFP after staining with FITC-labeled antibody, panel 2220 is a fluorescence image of luciferase after staining with Rhodamine-labeled antibody, and panel 2222 is a merged fluorescence image of eGFP and luciferase. As shown in FIGS. 21 and 22, nearly 100% of cells showed strong signals for all three markers, demonstrating that the T4 nanoparticles efficiently delivered two different genes as well as large oligomeric complexes into dendritic cells. The same was observed using a series of other proteins displayed on the head, including the protective antigen from *B. anthracis*, F1-V fusion protein from *Yersinia pestis*, a gp140 envelope trimers from HIV-1.

In Vivo T4 Delivery

Figure 23:
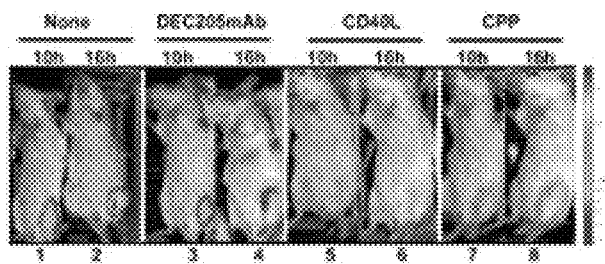
FIG. 23 is a series of images showing mice that were injected intramuscularly with T4 heads packaged with pLuci plasmid and its outer surface decorated either with no ligand or with DEC205mAb, CD40L, or CPP.
Figure 24:
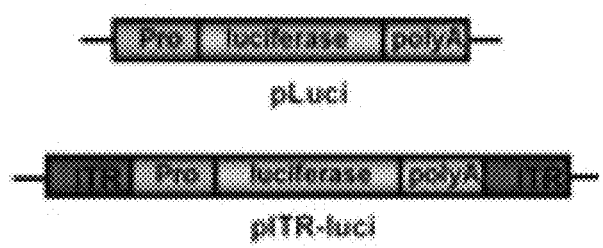
FIG. 24 is a schematic diagram of the luciferase expression cassettes used, without and with inverted terminal repeats (ITRs) from Adeno-associated virus (AAV), for packaging into T4 heads.
Figure 25:
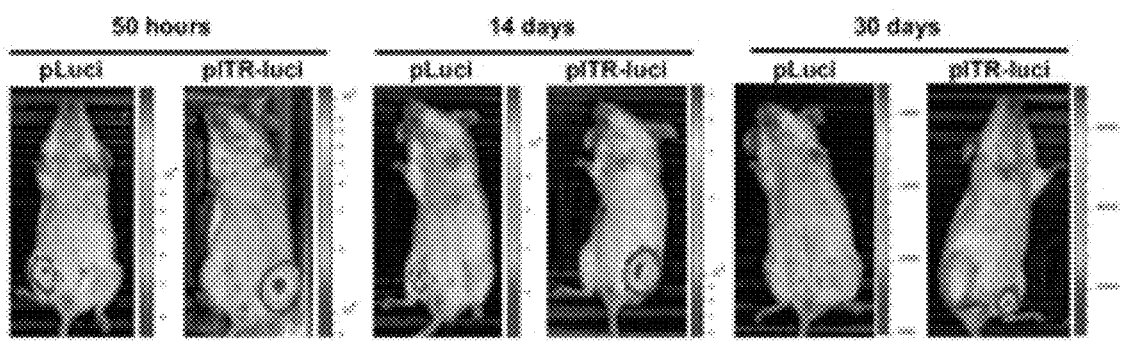
FIG. 25 is a series of images illustrating how the luciferase signal stays for a longer period of time if the expression cassette is flanked by ITRs.
Figure 26:
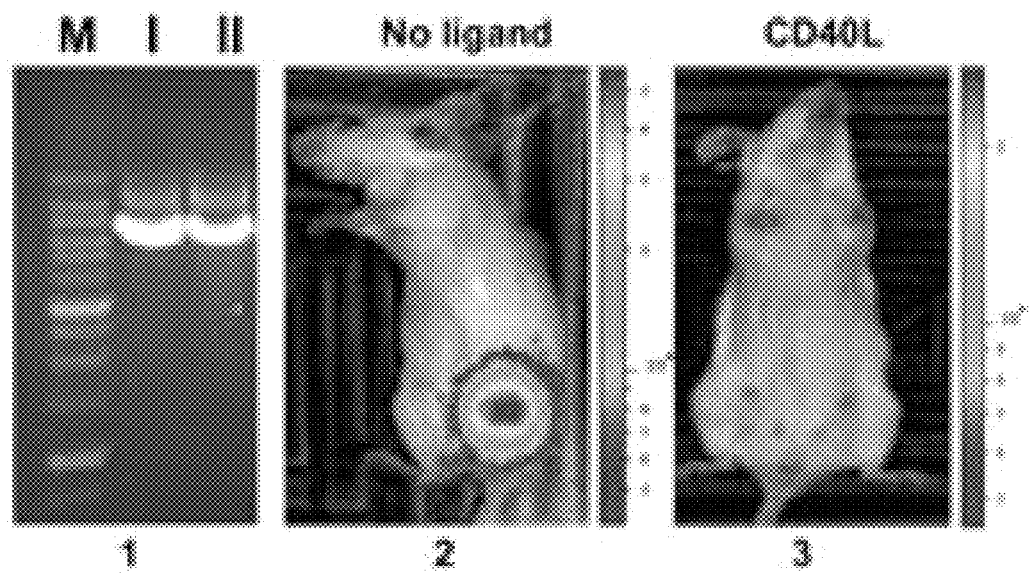
FIG. 26 is a series of images of further analysis of targeted delivery into dendritic cells.
Figure 27:
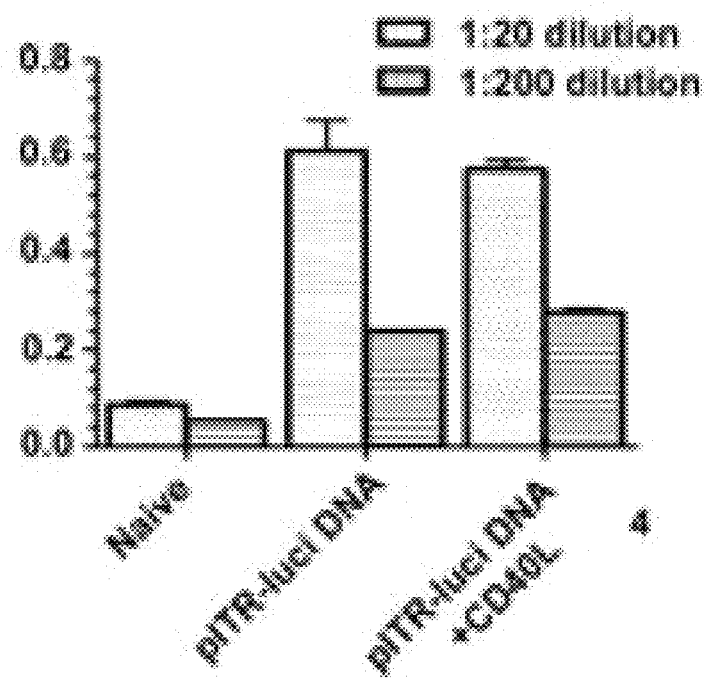
FIG. 27 is a graph of an ELISA titration showing that both the no-ligand group and the CD40L group induced the same level of anti-luciferase antibodies.
Figure 30:
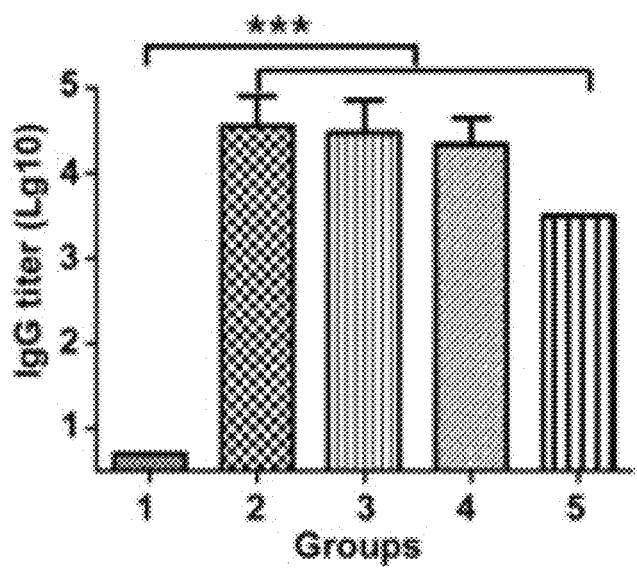
FIG. 30 is a bar graph showing results of the ELISA assays performed according to the procedures described in the present invention.
Figure 31:
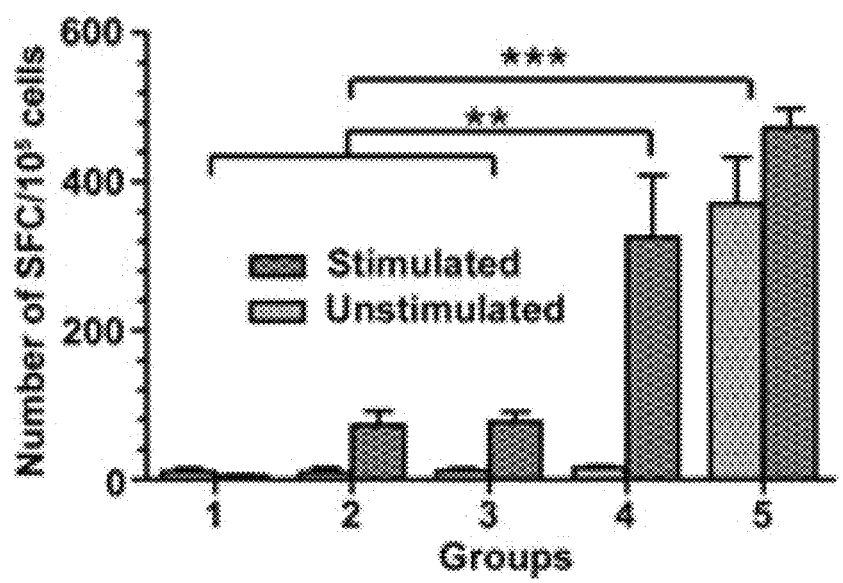
FIG. 31 is a bar graph showing results of the Elispot assays performed according to the procedures described in the present invention.

In another embodiment, in vivo T4 delivery was tested using a mouse model. Four groups of mice were injected intramuscularly with T4 heads packaged with the luciferase plasmid. The first group received heads containing no displayed ligand whereas the second, third and fourth groups received heads displayed with DEC205mAb, CD40L, and CPP-T, respectively. At different time points after injection, mice were injected with bioluminescence substrate D-Luciferin and the entire body was imaged. Unexpectedly, the strong luciferase signal was observed in the first group which received heads containing no displayed ligand (FIG. 23); these same particles showed very poor delivery in vitro (FIG. 7 and panel 1112 of FIG. 11). Furthermore, the signal appeared by as early as 6 hours after injection, suggesting that the muscle cells had taken up the T4 nanoparticles and expressed the delivered DNA efficiently at the site of injection. A time-course analysis showed that the luciferase signal was for at least 14 days using the standard luciferase expression cassette, and for at least 30 days if the cassette is flanked by AAV inverted terminal repeats (ITRs prime DNA replication of the delivered gene) (Asokan et al., 2012 (Reference 31)) (FIGS. 24 and 25). On the other hand, the DEC205mAb and CD40L displayed particles showed weak to no luciferase signal and the signal disappeared rapidly; by 16 hours, hardly any signal remained at the site of injection (FIG. 23, compare panels 3 and 4, 5 and 6, with 1 and 2). These data suggested that the dendritic cells that took up the DEC205mAb or CD40L displayed T4 particles migrated to other parts of the body, e.g., lymph nodes and spleen, thereby diluting signal to below the sensitivity of bioluminescence imaging (similar observations were made in a previous study (Yang et al., 2008) (Reference 32)). The CPP-displayed group also behaved similarly (FIG. 23, panels 7 and 8) but whether this was due to migration of dendritic cells and/or if other types of cells were also involved requires further investigation. To further confirm that the lack of signal was due to migration of dendritic cells rather than to lack of delivery, another control experiment was performed by delivering the same amount of luciferase DNA into mice using heads containing either no ligand or the displayed CD40L (FIG. 26, panel 2). In FIG. 26, panel 1 shows the same amount of pITR-luciferase was packaged into T4 heads decorated either with no ligand (lane I) or with CD40 (lane II); lane M shows molecular size standards. In panel 2 of FIG. 26, strong luciferase signal was seen at the site of injection with T4 heads containing no displayed ligand. In panel 3 of FIG. 26, no signal was seen at the site of injection with T4 heads displayed with the dendritic cell-specific ligand, CD40L. Moreover, the dendritic cell targeted group in addition elicited strong cellular immune responses (see below). Taken together, the above data demonstrate T4 delivery is efficient in vivo, and the delivery could be either localized to the muscle (although it could be secreted into the body by attaching a signal peptide) whereas in the targeted group, the gene product and the peptides derived from it travel, but importantly, are presented to dendritic cell-interacting cells such as the T cells and B cells (Steinman et al., 2007) (see below).

A Single Dose of T4 Delivered Plague Vaccine Induced Robust Humoral and Cellular Immune Responses An ideal vaccine would stimulate both the humoral (Th2) and cellular (Th1) arms of the immune system (Rappuoli et al., 2007 (Reference 33)). Delivering the vaccine in both forms, as antigen and as expressible DNA, might prime as well as boost the immune system ("prime-boost" vaccine), stimulating the Th1 and Th2 responses (Davtyan et al., 2009 (Reference 34)). This might be particularly important for combating complex infectious agents such as HIV-1, malaria, and TB for which no effective vaccines have yet been developed by traditional methods.

Plague, also known as Black Death, caused by *Yersinia pestis* might also require the induction of antibody and cellular immune responses (Smiley et al., 2008 (Reference 35)). The two principal candidates for plague vaccine are the capsular protein (Caf1 or F1, 16 kDa) and the low calcium response V antigen (LcrV or V, 37 kDa), a key component of the type 3 secretion system (Williamson et al., 2009 (Reference 36)). Current plague vaccines containing F1 and V recombinant proteins, elicit strong antibody responses but poor cellular immune responses (Do et al., 2008 (Reference 37)). This is a common problem encountered by conventional subunit vaccines (Carla et al., 2010 (Reference 38)). Disclosed embodiments of the present invention tested whether the T4 nanoparticles delivering both F1-V DNA and F1-V protein can modify the quality of immune responses. Furthermore, since the T4 delivered gene continues to be overexpressed for weeks, disclosed embodiments also tested if a single dose of vaccine would be sufficient to induce strong immune responses.

To execute the two aforementioned tests, a mutant F1-V gene that produces soluble monomeric F1-V fusion protein was cloned under the control of the strong CMV promoter. Then, the mutant F1-V protein was fused to the N-terminus of Soc and the fusion protein was displayed on the capsid surface. Groups of mice were immunized intramuscularly with a single dose of F1-V vaccine in various combinations (FIGS. 28 and 29). For prime-boost vaccination (group 5), mice were injected with T4 heads (~$5\times10^{11}$ particles) packaged with ~25 μg of F1-V DNA and displayed with ~30 μg of F1-V protein plus ~100 copies per head of DEC205mAb. Control groups included naive, F1-V protein adjuvanted with Alum, heads packaged with F1-V DNA, and heads displayed with F1-V protein. No adjuvant was included in any of the T4 vaccinated groups. ELISA of sera 4-weeks after immunization showed that strong antibody responses were induced in all the groups; end point titers as high as $7.5\times10^4$ were attained in some of the mice (FIG. 30). But strong cellular responses were elicited only in two of the groups, the T4 DNA group and the T4 prime-boost group that delivered both the F1-V DNA and the F1-V protein to dendritic cells (FIG. 31). Indeed, the latter group produced the strongest IFNγ response. Unexpectedly, splenocytes from this group showed high incidence of Elispots even without stimulation with F1-V antigen (FIG. 31; compare the red unstimulated column in group 5 with the same from rest of the groups). The counts increased further by F1-V stimulation (FIG. 31). These results are consistent with the hypothesis that T4 vaccine delivery into dendritic cells induces over-expression of F1-V and presentation to the immune system for a long period of time, in turn leading to continuous stimulation of T-cells.

The above results demonstrate the application of T4 progene delivery for prime-boost vaccination. Not only that a single dose of T4 vaccine without any adjuvant stimulated both arms of the immune system but also that, unlike the conventional vaccines, the immune system in T4 vaccinated animals remain activated for weeks after immunization. Thus, T4 appears to be a good platform for future development of efficacious prime-boost vaccines.

Conclusions

The above series of experiments established the phage T4 DNA packaging machine as a unique type of gene and protein delivery platform. With well understood structural and mechanistic features (FIG. 1); the 170-kb capacity head, the promiscuous packaging motor, the 1,025-molecule capacity surface lattice, Soc protein with exposed termini, and ~180 Å long Hoc fiber to capture target cells, T4 offers many options to engineer the nanoparticle for diverse applications. Unlike the existing systems that are mostly single featured and have limited capacity, the T4 applications range from simple in vitro delivery of genes and proteins to complex in vivo deliveries involving combinations of genes, proteins, oligomeric complexes and targeting molecules to treat diseases. A set of key experiments have been selected to demonstrate these broad applications. The data show that T4 efficiently delivered single or multiple genes, either as plasmids, PCR amplified DNAs, or concatemerized DNA. At the same time, single or multiple proteins were delivered, either as short peptides, full-length proteins, or large oligomeric complexes. Different parts of the nanoparticle were engineered to carry out different tasks but integrated to generate a desired outcome. For instance, one part (Hoc) was dedicated to target the nanoparticles to specific cells whereas another part (Soc) was designed to transiently express a new function, and yet another part (capsid interior) to overexpress an antigen for an extended period of time. Thus, T4 offers an advanced system for delivery of recombinant DNA and protein molecules.

The phage T4 platform offers several technical advantages that make it easily adaptable to any laboratory. Bacterially derived, the T4 is non-infectious, non-toxic, and has no preexisting immunity. The two main components of the T4 platform, heads and packaging motor (gp17), can be prepared relatively easily from *E. coli* in large quantities (~$5\times10^{13}$ heads, or 5 mg gp17, per liter of culture). Both are very stable, and retain activity after storage for at least two years at −70° C. The assembly steps are relatively simple, performed in a single tube, and completed in about 3 hours, and each step can be quantified. As shown, a series of customized nanoparticle with different compositions of genes and proteins could be prepared in a single experiment.

T4 progene delivery offers new avenues for developing useful biomedical therapies. Disclosed embodiments have demonstrated a prime-boost vaccination approach against pneumonic plague that elicits strong antibody and cellular immune responses. This approach could be used broadly to develop efficacious vaccines against infectious agents such as HIV-1, malaria, and TB. T4 heads delivering recombinase and targeting molecules displayed outside, and genomic DNA and siRNA genes packaged inside, could be used in cancer therapy, either to kill cancer cells by induction of apoptosis or to reverse the cancer phenotype by turning off certain oncogenes (Leuschner et al., 2011 (Reference 39)). T4 delivery might allow safe and efficient reprogramming of pluripotent stem cells by delivering transcription factor genes and proteins such as c-Myc, Klf4, Sox2 and Oct3/4, as well as replacing the defective gene with a functional gene by in vivo delivery of a long stretch of genomic DNA (Miki et al., 2012 (Reference 40)).

EXAMPLES

Example 1

Purification of 10-Amber13-Amber Hoc (Highly Antigenic Outer Capsid Protein)-Del.Soc (Small Outer Capsid Protein)-Del Heads The 10-amber13-amber.hoc-del.soc-del mutant was constructed by standard genetic crosses. *Escherichia coli* P301 (sup-) cells (500 mL) infected with this mutant were lysed in 40 mL of Pi-Mg buffer (26 mM Na2HPO4/68 mM NaCl/22 mM KH2PO4/1 mM MgSO4, pH 7.5) containing 10 μg/mL DNaseI and chloroform (1 mL) and incubated at 37° C. for 30 min. The lysate was subjected to two low-speed (6,000×g for 10 min) and high-speed (35,000×g for 45 min) centrifugations, and the final heads pellet was resuspended in 200 μL of Tris.Mg buffer (10 mM Tris.HCl, pH 7.5/50 mM NaCl/5 mM $MgCl_2$) and purified by CsCl density gradient centrifugation. The major head band sedimented at about ⅓ from the bottom of a 5-mL gradient was extracted and dialyzed overnight against Tris.Mg buffer. The heads were further purified by DEAE-Sepharose chromatography (Neumann et al., 2011). The peak heads fractions were concentrated and stored at −80° C.

Example 2

In Vitro DNA Packaging

In vitro DNA packaging assays were performed by the procedure described earlier (Kay, 2011). The reaction mixture contained purified Hoc⁻Soc⁻ heads [or wild type (WT) heads where indicated] (~2×1010 particles), purified gp17 (~1.5 µM), and DNA (~300 ng) using a buffer containing 30 mM Tris.HCl (pH 7.5), 100 mM NaCl, 3 mM $MgCl_2$, and 1 mM ATP. The DNA was a linearized molecule produced by digestion with a restriction enzyme. Examples include the MluI-linearized 4.7-kb pEGFP-C1 plasmid containing eGFP expression cassette and the BamHI-linearized 6.2-kb psiCHECK2 plasmid containing luciferase expression cassette. In some experiments, either the PCR-amplified 2.3-kb DNA corresponding to the expression cassettes or the ~80-kb ligated plasmid concatemer were used as a packaging substrate. The packaging reactions were terminated by the addition of DNaseI to digest the unpackaged DNA. The encapsidated and DNase I-resistant DNA was released by treatment with proteinase K and analyzed by agarose gel electrophoresis. The packaged DNA was quantified by Quantity One software. Each experiment included one to several negative controls that lacked one of the essential packaging components; heads, gp17, ATP, or DNA. Packaging efficiency is defined as the number of DNA molecules packaged per number of head particles used in the packaging reaction.

Example 3

In Vitro Display on Hoc⁻Soc⁻ T4 Heads

In vitro display of fusion proteins on T4 capsids was carried out as described (Demayo et al. 2012; Yan et al., 2010). After packaging luciferase and/or eGFP DNA as described above, the Hoc⁻Soc⁻ T4 heads (2-3×1010 particles) were incubated with Soc and/or Hoc fusion proteins in the same tube for 30 min at 4° C. for Soc fusions and 37° C. for Hoc fusions. For the display of DEC205mAb, the Hoc- or Soc-fused GG domain and the mAb were simultaneously added to the reaction mixture. The ratio of fusion protein to the respective binding sites on the capsid was adjusted. The binding sites on the capsid are occupied by the fusion proteins, decorating the head with one protein or a combination of proteins included in the reaction mixture. The heads were spun down for 45 min at 34,000×g, and the unbound proteins were removed by washing twice with 20 mM Tris.HCl (pH 8.0) and 100 mM NaCl. The head pellets were resuspended with Opti-MEM for transduction or with PBS (pH7.4) for SDS/PAGE analysis. The gels were stained with Coomassie blue 8250 and the protein bands were quantified by laser densitometry. The density of Hoc, Soc, gp23*, and gp18 (major tail sheath protein; 70 kDa) bands were determined for each lane separately and the number of bound Hoc or Soc molecules per capsid was calculated using the known copy numbers of gp23* (930 copies per head) or gp18 (138 copies per phage). A saturation binding curve relating the number of bound Soc molecules per capsid (Y) and the concentration of unbound protein in the binding reaction (X) was not sigmoidal, indicating that there is no cooperativity between neighboring Hoc or Soc binding sites. The apparent $K_d$ (association constant) and $B_{max}$ (maximum copies of Soc bound per capsid) were determined using the equation $Y=B_{max}X/(K_d+X)$ as programmed in the GraphPad PRISM-4 software.

Example 4

Gene Delivery for T4 Heads

Cells (2×105 cells per well for HEK293T and Hep3B, 1.5×105 cells per well for DC2.4) were seeded into a 24-well plate and incubated at 37° C. overnight in 5% (vol/vol) $CO_2$. The medium was then replaced with 500 µL of opti-MEM medium and 100 µL of engineered T4 heads (2×1010 heads for HEK293T or Hep3B cells or 1.5×1010 heads for DC2.4 cells or as indicated in figures) were directly added into each well. After incubation for 24 hours, luciferase expression was quantified as per the standard protocol. No significant difference in the luciferase signal was observed when the medium was changed after only 2 h incubation. The cells were then washed with PBS and lysed by adding 160 µL per well of passive lysis buffer and shaking for 30 min at room temperature. A 20 µL aliquot of each lysate was transferred to a 96-well white plate and mixed with 100 µL of LARII buffer. The luminescence signal was detected by luminometer. In parallel, the same amount of cell lysate was analyzed for β-actin by Western blotting using β-actin to confirm that the same number of cells was taken for each assay.

Example 5

Protein Delivery by T4 Heads

β-galactosidase-Soc was incubated with Hoc⁻Soc⁻ T4 heads for 45 min at 4° C. Hoc-T or Hoc-GG and DEC205 mAb were added to the same reaction tube and incubated for another 45 min at 4° C. The heads were spun down for 45 min at 34,000×g, and the unbound proteins were removed by washing twice with the buffer as described above. The head pellets were resuspended in opti-MEM for transduction or PBS for determination of β-galactosidase activity. For the latter, X-Gal was added to the tube and incubated for 10 min at room temperature. Delivery was carried out as described above and the β-galactosidase activity was visualized by microscopy at 3 or 24 h after adding heads by staining with X-Gal using the β-galactosidase staining kit.

Example 6

Single-Molecule Optical Tweezers DNA Packaging

Packaging by single packaging machines using optical tweezers packaging was performed to the procedure described earlier (Kaczmarczyk et al., 2011; Smith et al., 2001). Purified heads (4×109 particles) were mixed with purified gp17 (1 µM) and 125-bp "priming" DNA (0.44 µM) in the presence of 1 mM ATP-γ-S in a 10-4, reaction volume consisting of packaging buffer (50 mM Tris.HCl, pH 7.6/100 mM NaCl/5 mM MgCl2). After incubation at 37° C. for 30 min, T4 phage antibody-coated polystyrene beads (1.5 µL) (0.79 µm in diameter, Spherotech) were added. The DNA beads were prepared by adding PCR-amplified 10-kb λ DNA biotinylated at one end to the Streptavidin coated polystyrene beads (0.86 µm in diameter, Spherotech) and incubating at 37° C. for 30 min. Measurements were taken using a calibrated dual-trap optical tweezers at 100 Hz in a "force-feedback" mode, where packaging was allowed to occur against a constant force of 5 pN. Tether formation and packaging was initiated by infusing 1 mM ATP into the flow cell. The contour length of DNA was calculated from the measured force and extension between the beads using the worm-like chain model assuming a persistence length of 53 nm, a stretch modulus of 1,200 pN/nm, and distance per base pair of 0.34 nm. The velocity of DNA packaging was determined from a linear fit of the contour f DNA over a sliding window of 0.1 s (10 data points).

Example 7

Single-Molecule Fluorescence DNA Packaging

The single-molecule packaging of fluorescently labeled oligonucleotide was performed according to the basic procedure described earlier (Neumann et al. 1982). The individual T4 packaging machines were immobilized through T4 phage anti-body attached to the PEG surface-passivated coverslips. The unbound heads were washed off and ATP and 39 bp Cy5 DNA in the packaging buffer were flowed in [50 mM Tris.HCl buffer, pH 8.0/5% (wt/vol) PEG/5 mM $MgCl_2$/1 mM spermidine/60 mM NaCl, and the oxygen scavenger system (0.8% dextrose/0.1 mg/mL glucose oxidase/0.02 mg/mL catalase, and 3 mM Trolox)]. Packaging of Cy5 DNA by single machines was imaged by a charged-coupled-device camera at 100-milli-second time resolution.

Example 8

Construction of Recombinant Plasmids

All of the cell penetration peptide (CPP) recombinant genes were amplified by two rounds of PCR. The first round of PCR was performed by fusing Hoc or Soc genes to a sequence containing the 12-amino acid linker and part of CPP. The PCR products were used as a template for the second round of PCR using an end primer containing the rest of the CPP sequence and an appropriate restriction site. The resulting fragments containing restriction enzyme site-CPP-linker-Hoc/Soc-restriction enzyme site were purified by agarose gel electrophoresis, digested with appropriate restriction enzymes, and ligated with the gel-purified pET-28b vector DNA digested with the same restriction enzymes. Insertion of the Hoc-fused DNA fragment resulted in in-frame fusion with a 23-amino acid vector sequence containing a hexa-histidine sequence at the N terminus. Insertion of the Soc-fused DNA fragment resulted in in-frame fusion with an 8-amino acid vector sequence containing a hexa-histidine sequence at the C terminus. For the rest of recombinant constructions (GG domain, β-galactosidase), Soc and Hoc were amplified individually with appropriate primers. The purified PCR products were digested with appropriate restriction enzymes. The three restriction-enzyme-digested fragments (for Hoc-GG: GG domain, pET-28b, and Hoc; for Soc-GG: GG domain, pET-28b, and Soc; for β-gal-Soc: β-galactosidase, pET-28b, and Soc) were directionally ligated to generate the appropriate fusion products. Insertion of the recombinant DNA resulted in in-frame fusion with a 23-amino acid vector sequence containing a hexa-histidine sequence at the N terminus and in the case of the Soc-fusions, a second hexa-histidine tag was also added to the C terminus of the recombinant. The ligated DNAs were transformed into *E. coli* XL10 Gold cells, miniprep plasmid DNAs were prepared from the transformants by alkaline lysis, and the sequence of each clone was confirmed by DNA sequencing. The recombinant DNAs were then transformed into the expression strain *E. coli* RIPL for IPTG-induced overexpression of the recombinant proteins.

Example 9

Purification of Recombinant Proteins

The recombinant proteins were purified according to the basic protocol described as follows. The BL21 (DE3) RIPL cells harboring the recombinant clones were induced with 1 mM IPTG for 2 h at 30° C. The cells were harvested by centrifugation (4,000×g for 15 min at 4° C.) and resuspended in 50 mL of HisTrap binding buffer (50 mM Tris.HCl, pH 8.0/20 mM imidazole/300 mM NaCl). The cells were lysed using French-press and the soluble fraction containing the His-tagged fusion protein was isolated by centrifugation at 34,000×g for 20 min. The supernatant was loaded onto a HisTrap column and washed with 50 mM imidazole containing buffer, and the protein was eluted with 20-500 mM linear imidazole gradient. The peak fractions were concentrated and purified by size exclusion chromatography using Hi-Load 16/60 Superdex-200 (prep-grade) gel filtration column in a buffer containing 20 mM Tris.HCl (pH 8.0) and 100 mM NaCl. The peak fractions were concentrated and stored at −80° C.

Example 10

Purification of DEC205 Monoclonal Antibody (mAb)

The hybridoma cell line HB-290 which produces rat IgG2a monoclonal antibody against DEC-205 was obtained from ATCC and grown at 37° C. in 5% (vol/vol) $CO_2$ with RPMI1640 supplemented with 10% (vol/vol) FBS. The mAb was purified from the supernatant by affinity chromatography on a Protein G column. The cell culture medium was centrifuged at low speed to remove the cell debris and the buffer composition of supernatant was adjusted to 20 mM sodium phosphate (pH 7) by passing through Tangential Flow Filtration System. The samples were then load onto the Protein G column and the mAbs were eluted with 0.1 M Glycine.HCl (pH 2.8). The mAb fractions were collected in tubes containing 80 μL of 1 M (pH 9) to neutralize the eluate and preserve the function of mAb.

Example 11

Adeno-Associated Virus (AAV) Vector Production

AAV serotype DJ kit, engineered by DNA family shuffling to create a hybrid capsid from eight different native serotypes was used in current study (Fuller et al., 2007). AAV-DJ vectors exhibit significantly higher infectivity rates compared with native serotypes across a broad range of tissue and cell types. The firefly luciferase gene was cloned into the AAV vector and the luciferase-AAV was produced by co-transfection into HEK293T cells using three-plasmids. Seventy hours after transfection, AAV was collected and purified according to the manufacturer's instructions. The AAV titer was determined by QuickTiter™ AAV Quantitation kit.

Example 12

Indirect Immunofluorescence Microscopy

Cells (4×105 cells per well for HEK293T and 3×105 cells per well for DC2.4) were seeded into two-chamber slides and incubated at 37° C. overnight in 5% (vol/vol) CO2 incubator. Twenty four hours after transduction, the cells were washed with PBS (pH7.4), and stained with X-Gal to check the β-galactosidase activity as described above. The cells were then further fixed with 4% (vol/vol) paraformaldehyde and permeabilized with 0.1% Surfact-Amps X-100. After incubation with goat anti-luciferase primary antibody (1:1,000 dilution) or mouse anti-GFP primary antibody (1:2,000 dilution) for 1 h at 37° C., the cells were probed with rhodamine-labeled rabbit anti-goat second antibody (1:1,000 dilution, KPL) or FITC-labeled rabbit anti-mouse second anti-body (1:2,000 dilution), respectively. The cells were imaged by an inverted AX10 Observer Dl microscope, and images of cells that exhibited β-galactosidase activity, eGFP fluorescence, and rhodamine fluorescence were acquired sequentially and analyzed with Axiovision™ software.

Example 13

ELISA

Each well of a 96-well plate was coated with 0.1 µg of protein diluted in coating buffer (0.05 M sodium carbonate-sodium bicarbonate, pH 9.6) overnight at 4° C. The plates were then blocked with 3% (wt/vol) BSA in PBS (pH 7.4) for 1 h at 37° C. Equal volumes of the serum samples were serially diluted with dilution buffer (PBS, pH 7.4, with 1% BSA) and added into each well. After 1-hour incubation at 37° C., plates were washed with washing buffer PBS-T (PBS with 0.1% Tween 20, pH 7.4). Sheep anti-mouse IgG-HRP (Invitrogen) diluted 1:2,000 in dilution buffer was used as second antibody. After incubation with second antibody for 1 h at 37° C., TMB Microwell Peroxidase Substrate System was used for color development and the reaction was stopped by adding TMB BlueSTOP (KPL) solution. The OD values at a wavelength of 650 nm were read by ELISA reader.

Example 14

Elispot

A total of 55 5- to 6-week-old Balb/cJ mice were vaccinated by the intramuscular route (i.m.) with phage T4 head particles containing F1-V DNA and or protein. At 21 days, spleens from three mice in each vaccinated group were harvested and splenocytes were isolated from each animal and pooled for each group. Splenocytes (106 per mL) were plated in triplicate and stimulated with 5 µg/mL of F1-V, recombinant mouse IFN-γ, or media, and incubated for 24 h at 37° C. The mouse IFN-γ ELIspot kit was used to determine the relative number of IFN-γ-expressing cells in the single-cell spleen suspensions following the manufacturer's instructions. The Immunospot Series 1 Analyzer Elispot Reader quantify the number of spot forming cells per well.

Example 15

Live Animal Imaging Series

About $2-5 \times 10^{11}$ head particles were injected into each Balb/cJ mice by the intramuscular route (i.m.). After 6 hours, 10 hours, 16 hours, 30 hours, 50 hours, 14 days, and 30 days postinjection, mice were injected intraperitoneally (i.p.) with 30 µg of RediJect D-Luciferin Ultra and, after 5 min, mice were subjected to in vivo imaging using an IVIS 200 bioluminescent and fluorescence whole-body imaging workstation (Caliper) after lightly anesthetizing the animals under isofluorane. The bio-luminescent scale is provided within the figures and it ranges intense (red) to least intense (violet) scaled based on radiance intensity.

Example 16

Statistical Analyses

Results are expressed as mean±SD. Statistical comparisons between two groups were evaluated by Student t test and corrected by ANOVA for multiple comparisons. A value of $P<0.05$ was considered to indicate statistical significance.

While the present invention has been disclosed with references to certain embodiments, numerous modification, alterations, and changes to the described embodiments are possible without departing from the sphere and scope of the present invention, as defined in the appended claims. Accordingly, it is intended that the present invention not be limited to the described embodiments, but that it has the full scope defined by the language of the following claims, and equivalents thereof.

REFERENCES

The following references are referred to above and/or describe technology that may be used with the present invention and contents and disclosures of the following references are incorporated herein by reference:

1. Neumann, E, Schaefer-Ridder M, Wang Y, and Hofschneider P H Gene transfer into mouse lyoma cells by electroporation in high electric fields. *EMBO J* 1(7):841-45 (1982).
2. Kay M A State-of-the-art gene-based therapies: the road ahead. *Nat Rev Genet* 12(5):316-328 (2011).
3. Demayo J L, Wang J, Liang D, Zhang R, and Demayo F H Genetically engineered mice by pronuclear DNA microinjection. *Curr Protoc Mouse Biol* 2:245-62 (2012).
4. Yan M, Du J, Gu Z, Liang M, Hu Y, Zhang W, Priceman S, Wu L, Zhou Z H, Liu Z et al. A novel intracellular protein delivery platform based on single-protein nanocapsules. *Nat Nanotechnol* 5(1):48-53 (2010).
5. Kaczmarczyk S J m Sitaraman K, Young H A, Hughes S H, and Chatterjee D K Protein delivery using engineered virus-like particles. *Proc Natl Acad Sci USA* 108(41): 16998-17003.
6. Smith D E, Tans S J, Smith S B, Grimes S, Anderson D L, and Bustamante C The bacteriophage straight phi29 portal motor can package DNA against a large internal force. *Nature* 413(6857):748-52(2001).
7. Fuller D N, Raymer D M, Kottadiel V I, Rao V B and Smith D E Single phage T4 DNA packaging motor exhibit large force generation, high velocity, and dynamic variability. *Proc Natl Acad Sci USA* 104(43):16868-73 (2007).
8. Casjens S R The DNA-packaging nanomotor of tailed bacteriophages. *Nat Rev Microbiol* 9(9):647-57 (2011).
9. Rao V B and Feiss M The bacteriophage DNA packaging motor. *Annu Rev Genet* 42:647-81 (2008).
10. Sun S, Kondabagil K, Draper B, Alam T I, Bowman V D, Zhang Z, Hegde S, Fokine A, Rossmann M G, and Rao V B The structure of the phage T4 DNA packaging motor suggests a mechanism dependent on electrostatic forces. *Cell* 135(7):1251-62 (2008).
11. Fokine A, Chipman P R, Leiman P G, Mesyanzhinov V V, Rao V B, and Rossmann M G Molecular architecture of the prolate head of bacteriophage T4. *Proc Natl Acad Sci USA* 101(16):6003-08 (2004).
12. Black L W, Showe M K, and Steven A C Morphogenesis of the T4 Head, ed. Karam J D. *American Society of Microbiology, Washington D.C.* pp 218-58 (1994).
13. Qin L, Fokine A, O'Donnell E, Rao V B, and Rossmann M G Structure of the small outer capsid protein, Soc: a clamp for stabilizing capsids of T4-like phages. *J Mol Biol* 395 (4):728-41 (2010).
14. Fokine A, Islam M Z, Zhang Z, Bowman V D, Rao V B, and Rossmann M G Structure of the three N-terminal immunoglobulin domains of the highly immunogenic outer capsid protein from a T4-like bacteriophage. *J Virol* 85(16):8141-48 (2011).
15. Ishii T and Yanagida M The two dispensable structural proteins (soc and hoc) of the T4 phage capsid; their purification and properties, isolation and characterization of the defective mutants, and their binding with the defective heads in vitro. *J Mol Biol* 109(4):487-514 (1977).
16. Li Q, Shivachandra S B, Leppla S H, and Rao V B Bacteriophage T4 capsid: a unique platform for efficient surface assembly of macromolecular complexes. *J Mol Biol* 363(2):577-88 (2006).
17. Sathaliyawala T, Rao M, Maclean D M, Birx D L, Alving C R, and Rao V B Assembly of human immunodeficiency virus (HIV) antigens on bacteriophage T4: a novel in vitro approach to construct multicomponent HIV vaccines. *J Virol* 80(15):7688-98 (2006).
18. Zhang Z, Kottadiel V I, Vafabakhsh R, Dai L, Chemla Y R, Ha T, and Rao V B A promiscuous DNA packaging machine from bacteriophage T4. *PLoS Biol* 9(2):e1000592 (2011).
19. Leiman P G, Arisaka, F, van Raaig M J, Kostyuchenko V A, Aksyuk A A, Kanamaru S, and Rossmann M G Morphogenesis of the T4 tail and tail fibers. *VIrol J* 7:355 (2010).
20. Lander G C, Tang L, Casjens S R, Gilcrease E B, Prevelige P, Poliakov A, Potter C S, Carragher B, and Johnson J E The structure of an infectious P22 virion shows the signal for headful DNA packaging. *Science* 312(5781):1791-95 (2006).
21. Frankel A D and Pabo, C O Cellular uptake of the tat protein from human immunodefiency virus *Cell* 55(6): 1189-93 (1988).
22. Joliot A, Pernelle C, Deagostini-Bazin H, and Prochiantz A Antennapedia homeobox peptide regulates neural morphogenesis. *Proc Natl Acad Sci USA* 88(5):1864-68.
23. Grimm D, Lee J S, Wang L, Desai T, Akache B, Storm T A, and Kay M A In vitro and in vivo gene therapy vector evolution via multispecies interbreeding and retargeting of adeno-associated viruses. *J Virol* 82(12):5887-911.
24. Steinman R M and Banchereau J Taking dendritic cells into medicine. *Nature* 449(7161):419-26 (2007).
25. Bonifaz L C, Bonnyay D P, Charalambous A, Darguste D I, Fujii S, Soares H, Brimnes M K, Moltedo B, Moran T M, and Steinman R M In vivo targeting of antigens to maturing dendritic cells via the DEC-205 receptor improves T cell vaccination. *J Exp Med* 199(6):815-24 (2004).
26. Jiang W, Swiggard W J, Heufler C, Peng M, Mirza A, Steinman R M, and Nussenzweig M C The receptor DEC-205 expressed by dendritic cells and thymic epithelial cells is involved in antigen processing. *Nature* 375(6527):151-55.
27. van Kooten C and Banchereau J C D40-CD40 ligand *J Leukoc Biol* 67(1):2-17 (2000).
28. Akerstrom B, Brodin T, Reis K, and Bjorck L Protein G: a powerful tool for binding and detection of monoclonal and polyclonal antibodies. *J Immunol* 135(4):2589-92 (1985).
29. Shen Z, Reznikoff G, Dranoff G, and Rock K L Cloned dendritic cells can present exogenous antigens on both MHC class I and class II molecules. *J Immunol* 158(6): 2723-30.
30. Jacobson R H, Zhang X J, DuBose R F, and Matthews B W Three-dimensional structure of beta-galactosidase from *E. coli. Nature* 369(6483):761-66 (1994).
31. Asokan A, Schaffer D C, and Samulski R J The AAV vector toolkit: poised at the clinical crossroads. *Mol Ther* 20(4):699-708 (2012).
32. Yang L, Yang H, Rideout K, Cho T, Joo K I, Ziegler L, Elliot J, Walls A, Yu D, Baltimore D, et al. Engineered lentivector targeting of dendritic cells for in vivo immunization. *Nat Biotechnol* 26(3):326-34 (2008).
33. Rappuoli R Bridging the knowledge gaps in vaccine design. *Nat Biotechnol* 25(12):1361-66 (2007).
34. Davtyan H, Mkrtichyan M, Movsesyan N, Petrushina I, Mamikonyan G, Cribbs D H, Agadjanyan M G, and Ghochikyan A DNA prime-protein boost increased the titer, avidity and persistence of anti-Abeta antibodies in wild-type mice. *Gene Ther* 17(2):261-71 (2009).
35. Smiley S T Immune defense against pneumonic plague. *Immunol Rev* 225:256-71 (2008).
36. Williamson E D Plague. *Vaccine* 27 Suppl 4:D56-60 (2009).
37. Do Y, Park C G, Kang Y S, Park S H, Lynch R M, Lee H, Powell B S, and Steinman R M Broad T cell immunity to the LcrV virulence protein is induced by targeted delivery to DEC-205/CD205-positive mouse dendritic cells. *Eur J Immunol* 38(1):20-29 (2008).
38. Carla M S R, and Virgil E Vaccine adjuvant methods and protocols ed. Davies G (Humana Press, New York), pp. 1-15 (2010).
39. Leuschner F, Dutta P, Gorbatov R, Novobrantseva T I, Donahoe J S, Courties G, Lee K M, Kim J I, Markmann J F, Marinelli B, et al. Therapeutic siRNA silencing in inflammatory monocytes in mice. *Nat Biotechnol* 29(11): 1005-10 (2011).
40. Miki K, Uenaka H, Saito A, Miyagawa S, Sakaguchi T, Higuchi T, Shimizu T, Okano T, Yamanaka S, and Sawa Y Bioengineered myocardium derived from induced pluripotent stem cells improves cardiac function and attenuates cardiac remodeling following chronic myocardial infarction in rats. *Stem Cells Transl Med* 1(5)430-37 (2012).
41. Rossmann M G, Mesyanzhinov V V, Arisaka F, and Leiman P G The bacteriophage T4 DNA injection machines. *Curr Opin Struct Biol* 14(2):171-80 (2004).
42. Lata R, Conway J F, Cheng N, Duda R L, Hendrix T W, Wikoff W R, Johnson J E, Tsuruta H, and Steven A C Maturation dynamics of a viral capsid: visualization of transitional intermediate states. *Cell* 100(2):253-63 (2000).

All documents, patents, journal articles and other materials cited in the present application are incorporated herein by reference.

While the present invention has been disclosed with references to certain embodiments, numerous modification, alterations, and changes to the described embodiments are possible without departing from the sphere and scope of the present invention, as defined in the appended claims. Accordingly, it is intended that the present invention not be limited to the described embodiments, but that it has the full scope defined by the language of the following claims, and equivalents thereof.

What is claimed is:

1. A method comprising the following steps:
packaging one or more DNA molecules into a Soc⁻Hoc⁻ phage T4 head to form a DNA packaged head, and
exposing the DNA packaged head to one or more Hoc fusion proteins and/or one or more Soc fusion proteins to form a phage T4 DNA packaging machine that comprises the DNA packaged head and the one or more Hoc fusion proteins and/or the one or more Soc fusion proteins displayed on surface of the DNA packaged head,
wherein the Soc⁻Hoc⁻ phage T4 head retains a portion of a genome DNA and is bound by a gp17 packaging motor, and
wherein the one or more Hoc fusion proteins comprise a dendritic cell specific ligand CD40L fused to Hoc and the one or more Soc fusion proteins comprise a dendritic cell specific ligand CD40L fused to Soc.

2. The method according to claim 1, wherein the method comprises conducting the following step prior to step (a):

binding the gp17 packaging motor at a vertex portal protein gp20 of a $Soc^-Hoc^-$ phage T4 head.

3. The method according to claim 1, wherein the one or more DNA molecules comprise two or more different foreign genes.

4. The method according to claim 3, wherein the two or more different genes are the genes for luciferase and green fluorescent protein (GFP).

5. A phage T4 DNA packaging machine made according to the method of claim 1.

6. A product comprising a phage T4 DNA packaging machine comprising:

a $Soc^-Hoc^-$ phage T4 head that retains a portion of a genome DNA and is bound by a gp17 packaging motor, one or more DNA molecules packaged in the $Soc^-Hoc^-$ phage T4 head, one or more Hoc fusion proteins and/or one or more Soc fusion proteins displayed on the surface of the $Soc^-Hoc^-$ phage T4 head, wherein the one or more Hoc fusion proteins comprise a dendritic cell CD40 ligand fused to Hoc and the one or more Soc fusion proteins comprise a dendritic cell CD40 ligand fused to Soc.

7. The product according to claim 6, wherein the one or more DNA molecules comprise two or more different genes.

8. The product according to claim 7, wherein the two or more different genes are the genes for luciferase and green fluorescent protein (GFP).

9. The method according to claim 1, comprising mixing the $Soc^-Hoc^-$ phage T4 head, gp17 packaging motor, ATP and the one or more DNA molecules in vitro to package the one or more DNA molecules into the $Soc^-Hoc^-$ phage T4 head.

10. The method according to claim 1, wherein the one or more DNA molecules comprise one or more plasmids, PCR amplified DNA, and/or concatemerized DNA.

11. The method according to claim 1, wherein a ratio of copy number of molecule of the one or more Hoc fusion proteins or of the one or more Soc fusion proteins to respective total number of Hoc or Soc binding sites on the surface of the DNA packaged head is adjustable.

12. The method according to claim 11, wherein a ratio of the copy number of molecule of the one or more Hoc fusion proteins or the one or more Soc fusion proteins to respective total number of Hoc or Soc binding sites on the surface of the DNA packaged head is 20:1.

13. The method according to claim 1, wherein the one or more DNA molecules comprise a recombinant F1-V gene from *Yersinia pestis*.

14. The method according to claim 1, wherein the one or more Hoc fusion proteins comprise Hoc fused to a recombinant F1-V protein from *Yersinia pestis*, and wherein the one or more Soc fusion proteins comprise Soc fused to a recombinant F1-V protein from *Yersinia pestis*.

15. A method comprising:

packaging one or more DNA molecules into a $Soc^-Hoc^-$ phage T4 head to form a DNA packaged head, and exposing the DNA packaged head to one or more Hoc fusion proteins and/or one or more Soc fusion proteins to form a phage T4 DNA packaging machine that comprises the DNA packaged head and the one or more Hoc fusion proteins and/or the one or more Soc fusion proteins displayed on surface of the DNA packaged head, wherein the $Soc^-Hoc^-$ phage T4 head retains a portion of a genome DNA and is bound by a gp17 packaging motor, wherein the one or more Hoc fusion proteins comprise a Hoc-GG fusion protein comprising an IgG binding domain of protein G fused to Hoc, wherein the one or more Soc fusion proteins comprise a Soc-GG fusion protein comprising an IgG binding domain of protein G fused to Hoc, and wherein a dendritic cell specific receptor monoclonal antibody is displayed on the surface of the DNA packaged head via binding to the Hoc-GG fusion protein and/or the Soc-GG fusion protein.

16. The method according to claim 15, wherein the one or more DNA molecules comprise two or more different foreign genes.

17. The method according to claim 15, wherein the one or more Hoc fusion proteins comprise Hoc fused to a recombination F1-V protein from *Yersinia pestis*, and wherein the one or more Soc fusion proteins comprise Soc fused to a recombinant F1-V protein from *Yersinia pestis*.

18. A method comprising:

packaging one or more DNA molecules into a $Soc^-Hoc^-$ phage T4 head to form a DNA packaged head, and exposing the DNA packaged head to one or more Hoc fusion proteins and/or one or more Soc fusion proteins to form a phage T4 DNA packaging machine that comprises the DNA packaged head and the one or more Hoc fusion proteins and/or the one or more Soc fusion proteins displayed on surface of the DNA packaged head, wherein the $Soc^-Hoc^-$ phage T4 head retains a portion of a genome DNA and is bound by a gp17 packaging motor, and wherein the one or more Hoc fusion proteins comprise a Hoc-CPP fusion protein and the one or more Soc fusion proteins comprise a Soc-CPP fusion protein.

19. The method of claim 18, wherein the Hoc-CPP fusion protein comprises Hoc-CPP-Tat and/or Hoc-CPP-Antp, and wherein the Soc-CPP fusion protein comprises Soc-CPP-Tat and/or Soc-CPP-Antp.

20. The method according to claim 18, wherein the one or more DNA molecules comprise two or more different foreign genes.

* * * * *